(12) United States Patent
Kampa et al.

(10) Patent No.: US 7,641,757 B2
(45) Date of Patent: Jan. 5, 2010

(54) METHOD OF MAKING A TUBULAR BODY FOR A CATHETER, SHEATH OR LEAD

(75) Inventors: Greg Kampa, Blaine, MN (US); Nicole Geiger, Plymouth, MN (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 12/144,547

(22) Filed: Jun. 23, 2008

(65) Prior Publication Data

US 2008/0251966 A1    Oct. 16, 2008

Related U.S. Application Data

(63) Continuation of application No. 11/330,501, filed on Jan. 12, 2006, now abandoned.

(51) Int. Cl.
| | |
|---|---|
| B29C 65/00 | (2006.01) |
| B32B 37/00 | (2006.01) |
| B29C 47/00 | (2006.01) |
| C08J 5/00 | (2006.01) |
| A61M 5/00 | (2006.01) |
| A61M 25/00 | (2006.01) |

(52) U.S. Cl. ............... 156/294; 156/86; 156/244.13; 156/308.2; 604/264

(58) Field of Classification Search ............ 256/84, 256/85, 86, 148, 149, 244.11, 244.13, 244.15, 256/244.24, 294, 308.2, 309.6, 293; 428/36.91; 604/102.02, 102.03
See application file for complete search history.

(56) References Cited

U.S. PATENT DOCUMENTS

| | | | |
|---|---|---|---|
| 4,627,439 A | 12/1986 | Harris | |
| 4,934,049 A | 6/1990 | Kiekhafer et al. | |
| 5,063,018 A * | 11/1991 | Fontirroche et al. | 264/514 |
| 5,115,818 A | 5/1992 | Holleman et al. | |
| 5,387,233 A | 2/1995 | Alferness et al. | |
| 5,527,325 A * | 6/1996 | Conley et al. | 606/159 |
| 5,662,606 A | 9/1997 | Cimino et al. | |
| 5,713,851 A * | 2/1998 | Boudewijn et al. | 604/35 |
| 5,792,401 A | 8/1998 | Burnham | |
| 5,796,044 A | 8/1998 | Cobian et al. | |
| 5,879,499 A * | 3/1999 | Corvi | 156/175 |
| 5,935,159 A | 8/1999 | Cross, Jr. et al. | |
| 6,249,708 B1 | 6/2001 | Nelson et al. | |
| 6,623,480 B1 | 9/2003 | Kuo et al. | |
| 6,721,604 B1 | 4/2004 | Robinson et al. | |
| 6,757,970 B1 | 7/2004 | Kuzma et al. | |
| 6,827,798 B1 * | 12/2004 | Ichikawa et al. | 156/73.1 |

(Continued)

OTHER PUBLICATIONS

NonFinal Office Action, mailed Jul. 9, 2007: Related U.S. Appl. No. 11/330,501.

(Continued)

*Primary Examiner*—Richard Crispino
*Assistant Examiner*—Brian R Slawski

(57) ABSTRACT

A method of forming a tubular body for a catheter, sheath or lead comprises extruding a polymer core having an integrally formed core wall, first lumen, and second lumen, placing a first layer over an outer circumferential surface of the extruded polymer core, and bonding the first layer to the circumferential surface of the extruded polymer cover via a reflow process. The first and second lumens are mandrel free during the reflow process, and a temperature of the reflow process is below a softening point of the polymer core to maintain a collapse free first and second lumen.

14 Claims, 19 Drawing Sheets

U.S. PATENT DOCUMENTS

| | | |
|---|---|---|
| 6,852,946 B2 | 2/2005 | Groen et al. |
| 2001/0015253 A1* | 8/2001 | Liska et al. ............ 156/244.13 |
| 2002/0147486 A1 | 10/2002 | Soukup et al. |
| 2003/0050681 A1 | 3/2003 | Pianca et al. |
| 2004/0020549 A1 | 2/2004 | Augscheller et al. |
| 2004/0039369 A1* | 2/2004 | Shelso ..................... 604/524 |
| 2004/0054349 A1* | 3/2004 | Brightbill .................. 604/524 |
| 2004/0064086 A1 | 4/2004 | Gottlieb et al. |
| 2004/0068240 A1* | 4/2004 | Goodin et al. .............. 604/264 |
| 2004/0097965 A1 | 5/2004 | Gardeski et al. |
| 2004/0116993 A1 | 6/2004 | Clemens et al. |
| 2006/0041293 A1 | 2/2006 | Mehdizadeh et al. |

OTHER PUBLICATIONS

Final Office Action, mailed Dec. 31, 2007: Related U.S. Appl. No. 11/330,501.

Advisory Action, mailed Apr. 22, 2008: Related U.S. Appl. No. 11/330,501.

NonFinal Office Action, mailed May 12, 2009: Related U.S. Appl. No. 11/745,728.

NonFinal Office Action, mailed May 22, 2009: Related U.S. Appl. No. 11/855,064.

* cited by examiner

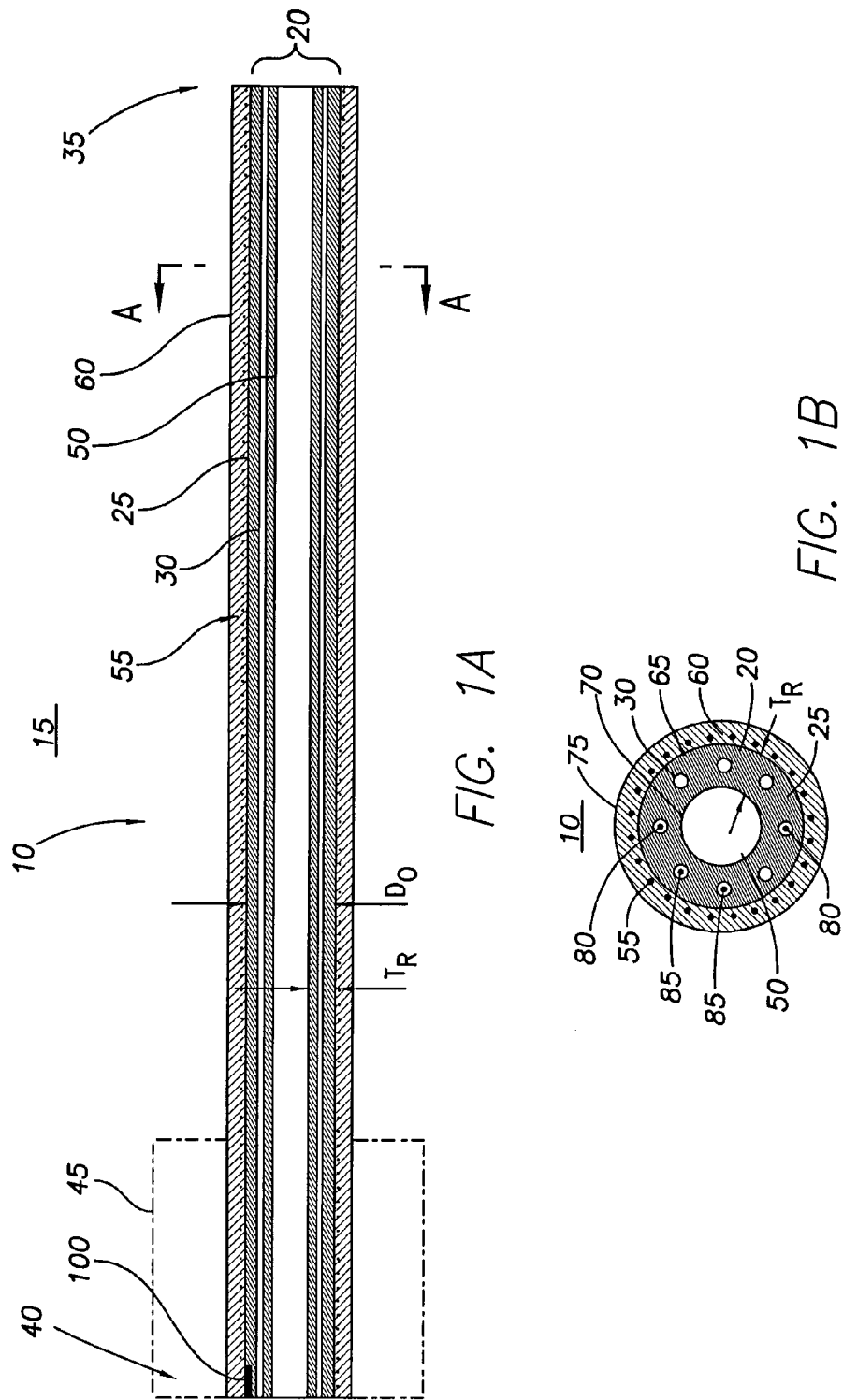

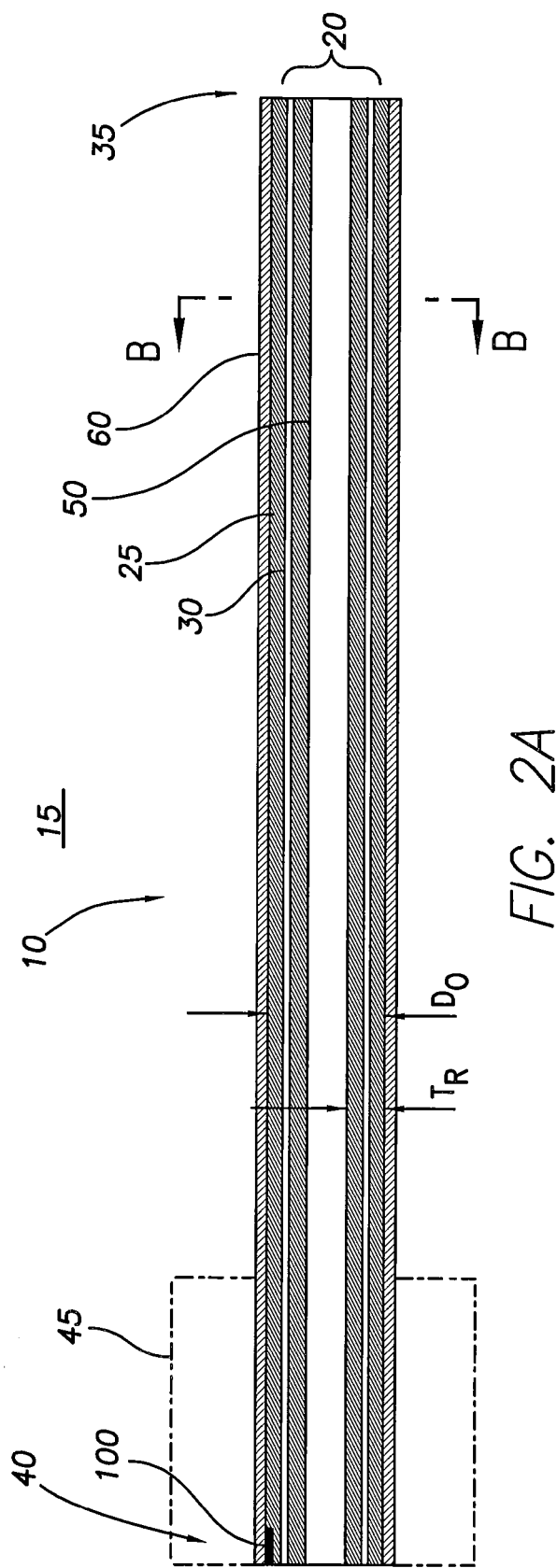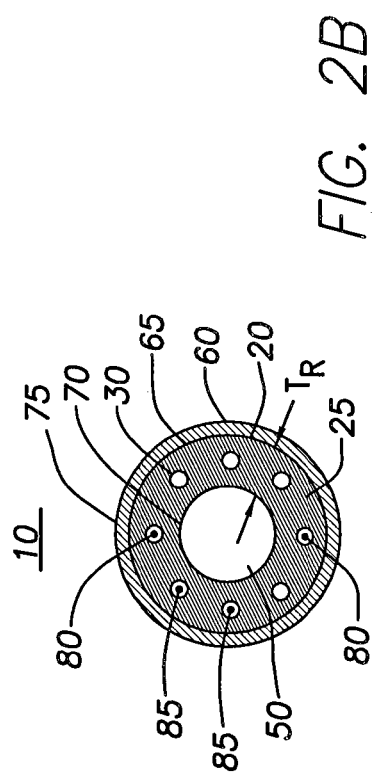
FIG. 2A
FIG. 2B

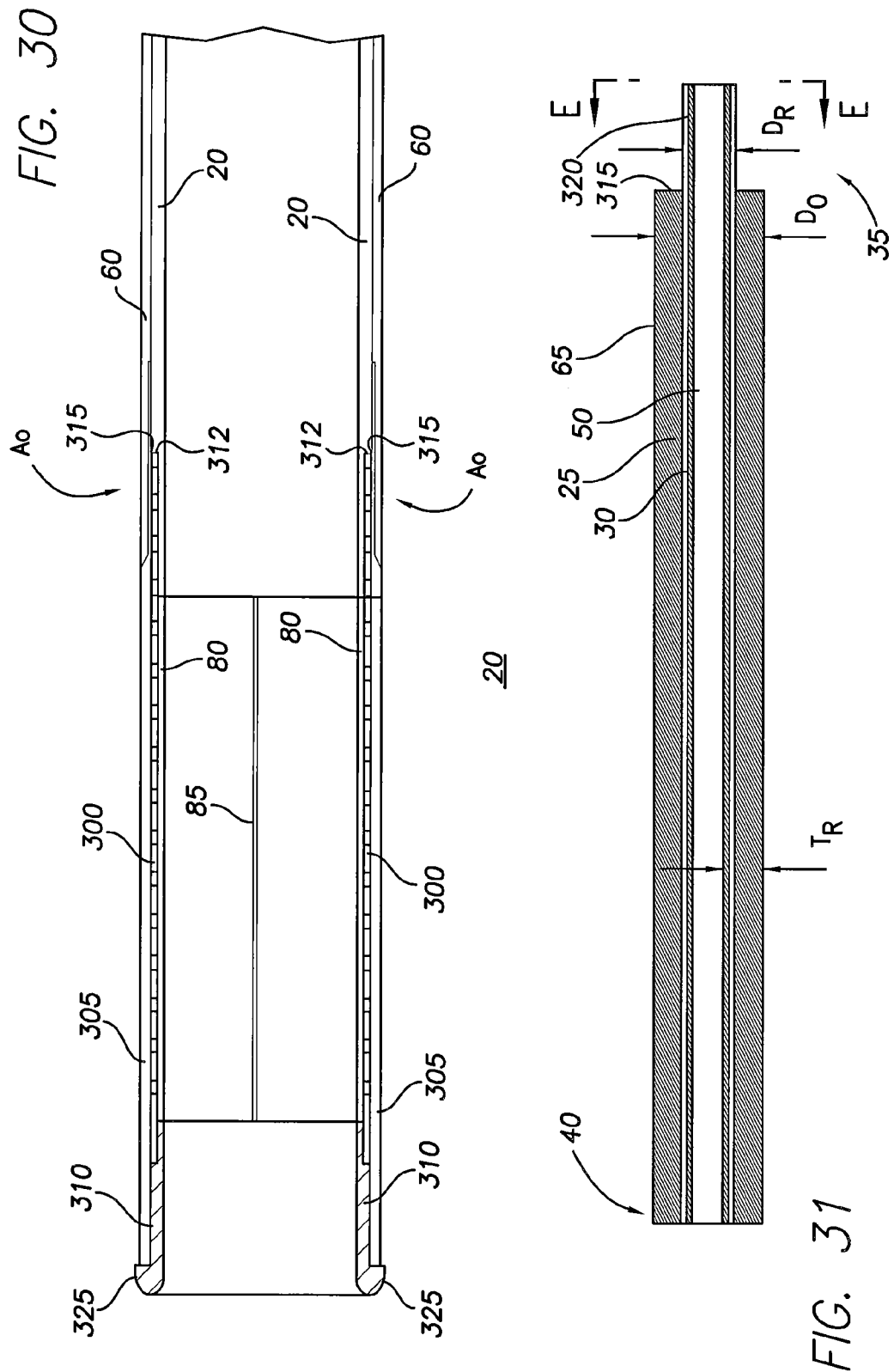

METHOD OF MAKING A TUBULAR BODY FOR A CATHETER, SHEATH OR LEAD

CROSS REFERENCE TO RELATED APPLICATIONS

This application is a continuation of copending U.S. patent application Ser. No. 11/330,501, filed Jan. 12, 2006, titled "Tubular Body for a Catheter, Sheath or Lead and Method of Making the Same."

FIELD OF THE INVENTION

The present invention relates to catheters, sheaths and leads and methods of making the same. More specifically, the present invention relates to the tubular bodies of catheters, sheaths and leads and methods of making such tubular bodies.

BACKGROUND OF THE INVENTION

In a variety of medical procedures, a tubular body of a catheter, sheath or lead (e.g., pacing lead) travels through a patient body lumen in route to a treatment site within the patient. A tubular body of a catheter or sheath will often include deflection wires that run the length of the tubular body through a central lumen of the tubular body. These deflection wires are used to deflect the distal end of the tubular body to facilitate the tubular body's negotiation of the patient body lumen or to facilitate the positioning of the tubular body's distal end adjacent to a treatment site.

Once positioned at the treatment site, the tubular body will be used to deliver a medical device (e.g., a pacemaker lead, a catheter, a stent, etc.) or a pharmaceutical to the treatment site, and/or the tubular body will be used to perform diagnostic and/or treatment procedures (e.g., RF ablation, deployment of a balloon to expand an occlusion, etc.) To enable the performance of diagnostic and/or RF ablation procedures, conductor wires are routed through the central lumen of the tubular body of a catheter, sheath or lead. To enable the delivery of a pharmaceutical, fluid conveying lumens are routed through the central lumen of the tubular body. To enable the delivery of a medical device, a medical device deploying lumen is routed through the central lumen of the tubular body.

Where a tubular body of a catheter, sheath or lead is adapted to perform one or more of the aforementioned procedures, the central lumen of such a tubular body becomes crowded with wires and/or lumens. The crowding makes it difficult to manufacture the tubular body because each wire and/or lumen must be threaded past the other wires and/or lumens previously installed in the tubular body's central lumen during the manufacturing process. The crowding can result in bent or kinked wires and lumens. The crowding makes the manufacture of the tubular bodies unnecessarily complicated and expensive.

The crowding within the central lumen increases the frictional resistance that must be overcome when displacing the deflection wires to cause the distal end of the tubular body to deflect. The crowding also increases the difficulty associated with passing a medical device through the tubular body to a treatment site. The crowding increases the difficulty associated with using the tubular body.

There is a need in the art for a tubular body that reduces the problems presented by the central lumen crowding associated with prior art tubular bodies. There is also a need in the art for a method of manufacturing a tubular body that is less complicated and, as a result, less expensive as compared to the methods used for prior art tubular bodies.

BRIEF SUMMARY OF THE INVENTION

The present invention, in one embodiment, a tubular body for a catheter, sheath or lead. The tubular body includes a longitudinally extending core, a central lumen, and several core wall lumens. The core is formed from polytetrafluoroethylene ("PTFE") and includes a core wall that, in one embodiment, has a radial thickness of at least approximately 0.003 inch. The radial wall thickness is generally constant along a circumference of the core wall. The central lumen is defined by the core wall. The core wall lumens longitudinally extend through the radial thickness of the core wall. The central lumen and core wall lumens are formed while extruding the core.

In one embodiment, the tubular body also includes a reinforcement layer and an outer polymer layer. The reinforcement layer extends about an outer circumferential surface of the core, and the outer polymer layer is bonded to said surface.

In one embodiment, the tubular body also includes a deflection wire and an electrical current conductor wire. The wires each extend through a core wall lumen. Additionally, one of the core wall lumens is as a fluid conveying conduit.

The present invention, in one embodiment, is a tubular body for a catheter, sheath or lead. The tubular body comprises a longitudinally extending polymer core, which includes a circumferential wall of a first thickness that is generally constant along the circumference of the wall. An inner circumferential surface of the wall defines a longitudinally extending central lumen. Another lumen longitudinally extends through the first thickness. A polymer layer of a second thickness circumferentially extends about, and is bonded to, an outer circumferential surface of the wall of the core. A reinforcement layer extends through the second thickness.

In one embodiment, the polymer layer is bonded to the outer circumferential surface of the wall via a reflow process. In one embodiment, the outer circumferential surface of the wall is etched to enhance the adhesion of the polymer layer to the outer circumferential surface.

In one embodiment, the polymer core is formed from PTFE. In one embodiment, the polymer layer is formed from a thermoplastic polymer (e.g., polyether block amide ("PEBAX"), nylon, polyurethane, etc. In another embodiment, the polymer layer is formed form a thermoset polymer (e.g., silicone, etc.). In one embodiment, the first thickness is between approximately 0.003 inch and approximately 0.03 inch. In one embodiment, the first thickness is at least approximately 0.003 inch.

In one embodiment, a deflection wire extends through the lumen longitudinally extending through the first thickness. In one embodiment, a conductor extends through the lumen longitudinally extending through the first thickness. The conductor is adapted to conduct a current between a distal end and a proximal end of the tubular body. In one embodiment, the lumen extending through the first thickness is adapted to communicate a fluid between a distal end and a proximal end of the tubular body.

The present invention, in one embodiment, is a method of manufacturing a tubular body for a catheter, sheath or lead. The method includes extruding a polymer core that has a core wall with at least one core wall lumen extending longitudinally through a radial thickness of the core wall. In one embodiment, the radial thickness of the core wall is at least approximately 0.003 inch, and the radial thickness of the core wall is generally constant about a circumference of the core wall. In one embodiment, a reinforcement layer is placed about an outer circumferential surface of the core and an outer polymer layer is bonded to said surface via a reflow process. Deflection and electrical conductor wires are inserted in their respective core wall lumens.

The present invention, in one embodiment, is a catheter, sheath or lead comprising a tubular body that includes a longitudinally extending polymer core, a reinforcement layer, and an outer polymer layer. The polymer core includes a core wall, a longitudinally extending central lumen defined by the core wall, and at least one core wall lumen extending longitudinally through a radial thickness of the core wall. The reinforcement layer extends circumferentially about an outer circumferential surface of the core, and the polymer layer extends circumferentially about the reinforcement layer.

In one embodiment, the polymer core is extruded and the central lumen and wall lumens are formed during the extrusion process In one embodiment, the polymer core is formed from PTFE.

In one embodiment, the catheter or sheath further comprises a wire extending through the core wall lumen. In one embodiment, the wire is a deflection wire for deflecting a distal end of the tubular body. In one embodiment, the wire is a conductor wire for conducting an electrical current along the length of the tubular body. In one embodiment, the core wall lumen serves as a fluid conveying conduit.

The present invention in one embodiment is a method of utilizing a catheter, sheath or lead during a medical procedure. The method comprises inserting a tubular body of the catheter, sheath or lead into a body of a patient. A core wall lumen longitudinally extends through a radial thickness of a core wall of the tubular body.

In one embodiment, a deflection wire extends through the core wall lumen. The deflection wire is displaced to cause a distal end of the tubular body to deflect. In one embodiment, a conductor wire extends through the core wall lumen. A current is caused to travel along the wire. The current is used to diagnose and/or treat a medical condition with the patient. In one embodiment, a fluid is displaced through the core wall lumen to remove fluid from the patient and/or to inject fluid into the patient.

The present invention, in one embodiment, is a method of assembling a catheter or sheath. The method comprises extruding a polymer core that has a core wall with at least one lumen longitudinally extending through a radial thickness of the core wall and wherein the core twists about a longitudinal axis of the core during the extrusion process. The method further comprises forming a tubular body of the catheter or sheath from the core and accounting for the twist when attaching the tubular body to a handle of the catheter or sheath.

In one embodiment, the polymer core is extruded from PTFE. In one embodiment, the twist causes an end of the lumen at the proximal end of the tubular body to be circumferentially offset from an end of the lumen at the distal end of the tubular body.

In one embodiment, the twist is accounted for by orienting the tubular body relative to the handle such that a distal end of tubular body displaces in an intuitive manner when a deflection wire actuator is displaced on the handle. In one embodiment, the twist is accounted for by routing a deflection wire through the lumen and coupling the proximal end of the tubular body to the handle as follows. The lumen is circumferentially offset at point of connection between the tubular body and the handle such that the twist brought about in the lumen over a length of the tubular body is accounted for such that a distal end of the tubular body displaces in a plane that is coplanar or parallel to a displacement plane of a deflection wire actuator.

The present invention, in one embodiment, is a tubular body of a catheter, sheath or lead. The tubular body comprises an extruded polymer core and a slot. The extruded polymer core includes a core wall and a core wall lumen longitudinally extending through a radial thickness of the core wall. The slot extends between the core wall lumen and an outer circumferential surface of the core. The polymer core is a PTFE core, and the slot is cut into the core via a laser.

In one embodiment, the tubular body further comprises a deflection wire and a deflection wire anchor member. The deflection wire extends through the lumen, and the deflection wire anchor member is coupled to a distal end of the tubular body. The wire and anchor are operably coupled to each other through the slot.

In one embodiment, the tubular body further comprises a balloon and a porous or perforated heat shrink material. The heat shrink material is placed over the slot and the balloon over the heat shrink material. To inflate the balloon, a fluid is communicated to the balloon via the lumen, the slot, and the porous or perforated heat shrink material. The heat shrink material is fluorinated ethylene-propylene copolymer ("FEP").

In one embodiment, a portion of the balloon is sandwiched between the core and an outer polymer layer via a reflow process. The outer polymer layer is a thermoplastic (e.g., PEBAX, nylon, polyurethane, etc.) or thermoset polymer (e.g., silicon, etc.).

The present invention, in one embodiment, is a method of manufacturing a tubular body for a catheter, sheath or lead. The method comprises extruding a polymer core and forming a slot in the core. When extruded, the polymer core includes a lumen longitudinally extending through a radial thickness of a wall of the core. The slot extends from an outer circumferential surface of the core to the lumen. In one embodiment, a deflection wire is fed through the slot and into the lumen. In one embodiment, the polymer core is a PTFE core.

In one embodiment, a porous or perforated shrink wrap material is placed over the slot, and a balloon is placed over the shrink wrap material. A polymer material layer then is reflowed over a portion of the balloon. The polymer material layer is a thermoplastic (e.g., PEBAX, nylon, polyurethane, etc.) or thermoset polymer (e.g., silicon, etc.).

The present invention, in one embodiment, is a method of joining a balloon to a tubular body of a catheter, sheath or lead. The method comprises placing a balloon material on a polymer core and reflowing a polymer material over a portion of the balloon material. The polymer core is PTFE and the polymer material is a thermoplastic (e.g., PEBAX, nylon, polyurethane, etc.) or thermoset polymer (e.g., silicon, etc.).

The present invention, in one embodiment, is a large diameter tubular body for a catheter or sheath, wherein a distal tip of the tubular body is deflectable. The tubular body comprises a polymer core, a cylindrical uniplanar spring, an elastomeric tube, an outer polymer tube and a wire. The polymer core includes a stepped distal end defined by a first outer diameter and a second outer diameter smaller than, and distal to, the first outer diameter. The polymer core further includes a core wall defining a central lumen and including at least one core wall lumen extending longitudinally through a radial thickness of the core wall. The cylindrical uniplanar spring is received around the second diameter. The elastomeric tube is received around the first outer diameter and spring. The outer polymer tube is reflowed around the first outer diameter and the elastomeric tube. The wire exits the at least one core wall lumen and extends distally adjacent an interior circumferential surface of the spring. In one embodiment, the wire is a conductor wire for transmitting an electrical current. In one embodiment, the wire is a deflection wire for deflecting the distal end of the tubular body.

The present invention, in one embodiment, is a method of manufacturing a large diameter tubular body for a catheter or sheath, wherein a distal tip of the tubular body is deflectable. The method comprises extruding a PTFE core having a first outside diameter, and forming a second outside diameter on a distal tip of the core, wherein the second diameter is smaller than, and distal to, the first diameter. The method further comprises placing a cylindrical uniplanar spring around the second diameter, placing an elastomeric tube around the first diameter and the spring, reflowing an outer polymer layer around the first diameter and the elastomeric tube, and running a wire through a lumen defined in a radial thickness of a core wall. The lumen is formed when the core is extruded.

The present invention, in one embodiment, is a method of peeling/splitting a tubular body of a catheter or sheath. The method comprises peeling/splitting the tubular body along a lumen extending longitudinally through a radial thickness of a core wall. The peeling/slitting of the tubular body begins at a score line aligned with the lumen.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1A is a longitudinal sectional elevation of a catheter, sheath or lead employing the tubular body of the subject invention, wherein the tubular body is reinforced with a reinforcement layer.

FIG. 1B is a cross-sectional elevation of the tubular body as taken along section line A-A in FIG. 1A.

FIG. 2A is a longitudinal sectional elevation of a catheter, sheath or lead employing the tubular body of the subject invention, wherein the core wall of the tubular body has a radial thickness that is sufficiently thick so as to not require the presence of the reinforcement layer of the embodiment depicted in FIGS. 1A and 1B.

FIG. 2B is a cross-sectional elevation of the tubular body as taken along section line B-B in FIG. 2A.

FIG. 30 is a longitudinal cross-sectional elevation of the distal end of a large diameter tubular body for a catheter or sheath. FIG. 31 is a longitudinal cross-sectional elevation of the core depicted in FIG. 30.

DETAILED DESCRIPTION

Overview

Figure 3:
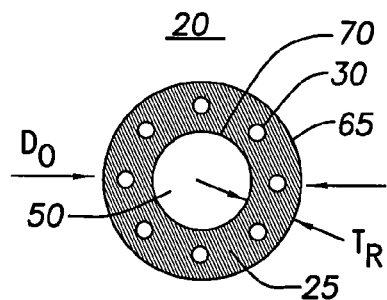
FIG. 3 is a cross-sectional elevation of a core subsequent to being extruded and prior to being combined with other components to form the tubular body, as if taken along section line A-A in FIG. 1A.

The present invention, in one embodiment, is a tubular body 10 of a catheter, sheath or lead (e.g., pacing lead) 15 and a method of manufacturing the tubular body 10. The tubular body 10 employs a longitudinally extending polymer core 20 that has a core wall 25 with a radial thickness $T_R$ that is sufficiently great to allow one or more core wall lumens 30 to longitudinally extend through the radial thickness $T_R$ of the core wall 25. This configuration is advantageous for several reasons. First, the functional components of the tubular body 10 (e.g., deflection wires for deflecting the distal end of the tubular body 10, conductor wires for transmitting an electrical current for medical condition diagnosis and/or treatment, lumens for conveying a fluid through the tubular body 10, and etc.) are routed through the core wall lumens 30. This leaves the central lumen 50 of the tubular body 10 free of obstruction for the introduction of medical devices into the central lumen 50 by the physician. Second, inserting the functional components into their respective core wall lumens 30 decreases the complexity associated with assembling the tubular body 10, as compared to trying to insert all of the functional components into the same central lumen 50. Third, in one embodiment, the core 20 of the subject invention facilitates the construction of an improved large diameter deflectable sheath or catheter having a deflectable distal end. Fourth, in one embodiment, the core 20 of the subject invention facilitates the construction of an improved balloon-type catheter. Fifth, in one embodiment, the core 20 of the subject invention facilitates the construction of an improved lead (e.g., pacing lead) that requires significantly less assembly steps than prior art leads and, in one embodiment, does not require the coils commonly found in prior art leads. Sixth, in one embodiment where the core 20 is extruded from PTFE and the radial thickness $T_R$ of the core wall 25 is sufficiently great, the tubular body 10 will not require a reinforcement layer 55. As a result, the resulting tubular body 10 will provide the strength/toughness of a typical tubular body while being readily splittable/peelable. Furthermore, such a tubular body 10 will be free of magnetic materials, thereby making possible interventional procedures utilizing magnetic resonance imagery ("MRI").

The tubular body 10 of the subject invention offers improved operability and decreased manufacturing costs. Also, the tubular body 10 of the subject invention offers a highly adaptable platform that can be used for a variety of catheters, sheaths and leads. For example, the tubular body 10 can be used to form MRI compatible catheters and sheaths, standard ablation catheters, diagnostic and guide catheters, introducers, dialators, balloon occlusion catheters, pacing leads, and etc.

Tubular Body

For a discussion of the tubular body 10 of the subject invention, reference is made to FIGS. 1A-2B. FIG. 1A is a longitudinal sectional elevation of a catheter, sheath or lead 15 employing the tubular body 10 of the subject invention, wherein the tubular body 10 is reinforced with a reinforcement layer 55. FIG. 1B is a cross-sectional elevation of the tubular body 10 as taken along section line A-A in FIG. 1A. FIG. 2A is a longitudinal sectional elevation of a catheter, sheath, or lead 15 employing the tubular body 10 of the subject invention, wherein the core wall 25 of the tubular body 10 has a radial thickness $T_R$ that is sufficiently thick so as to not require the presence of the reinforcement layer 55 of the embodiment depicted in FIGS. 1A and 1B. FIG. 2B is a cross-sectional elevation of the tubular body 10 as taken along section line B-B in FIG. 2A.

As shown in FIGS. 1A and 2A, the catheter, sheath or lead 15 includes a distal end 35 for entering into a patient and a proximal end 40 for manipulation by a physician. In one embodiment, where the tubular body 10 is part of a catheter or sheath 15, the tubular body 10 will include a handle 45 on the proximal end 40 for manipulation by a physician. As depicted in FIGS. 1A and 1B, in one embodiment, the tubular body 10 includes a polymer core 20, a reinforcement layer 55, and an outer polymer layer 60. As illustrated in FIGS. 2A and 2B, in one embodiment, the radial thickness $T_R$ of the core wall 25 is sufficiently thick such that the tubular body 10 does not require a reinforcement layer 55 to be sufficiently strong and durable.

As shown in FIGS. 1A-2B, the polymer core 20 includes a central lumen 50, a circumferentially continuous core wall 25, and one or more core wall lumens 30 longitudinally extending within the radial thickness $T_R$ of the core wall 25. The core wall 25 includes an outer circumferential surface 65 and an inner circumferential surface 70 that defines the central lumen 50. Where a reinforcement layer 55 is present, as shown in FIGS. 1A and 1B, the reinforcement layer 55 extends about the outer circumferential surface 65 of the core wall 25, and the outer polymer layer 60 impregnates the reinforcement layer 55. As indicated in FIGS. 1A-2B, the outer polymer layer 60 bonds to the outer circumferential surface 65 of the core wall 25. The polymer layer's outer circumferential surface 75 forms the outer circumferential surface of the tubular body 10.

As indicated in FIGS. 1A and 2A, the central lumen 50 and the one or more core wall lumens 30 extend from the distal end 35 to the proximal end 40. As illustrated in FIGS. 1B and 2B, the core wall lumens 30 extending through the core wall 25 are used for various purposes. For example, in one embodiment, a deflection wire 80 extends through a core wall lumen 30 from the proximal end 40, where the wire connects to the handle 45, to the distal end 35. Manipulating the handle 45 causes the wire 80 to displace within the core wall lumen 30, which causes the distal end 35 to deflect. In one embodiment, each deflection wire 80 has a diameter of between approximately 0.006 inch and approximately 0.009 inch.

In one embodiment, a conductor wire 85 extends through a core wall lumen 30 from the handle 45 to one or more electrical devices (e.g., electrodes or tracking coils) located at the distal end 35. The conductor wire 85 transmits an electrical current that is used to track the location of the tubular body 10 or diagnose and/or treat a medical condition. In one embodiment, the conductor wire 85 is a between approximately 38 gage and approximately 52 gage coaxial wire.

In one embodiment, a core wall lumen 30 serves as a conduit for transporting a fluid between the distal and proximal ends 35, 40 of the tubular body 10. For example, in one embodiment, a core wall lumen 30 serves as a conduit through which a fluid is delivered from the proximal end 40 to the distal end 40 for treatment of a medical condition. In one embodiment, a core wall lumen 30 serves as a conduit through which a fluid is transported from the distal end 35 to the proximal end 40. In one embodiment, a core wall lumen 30 is used to inflate or deflate an occlusion balloon near the distal end of the tubular body 10. Such a balloon is used to occlude a vein or artery during the performance of a medical procedure.

In one embodiment, a core wall lumen 30 is intermittently/partially or continuously/totally filled with a radiopaque marker material. The marker material is visible via x-ray fluoroscopy, which allows the positioning of the tubular body 10 to be ascertained during a medical procedure.

In one embodiment, the core wall lumens 30 are used as pathways through which medical instruments and devices (e.g., micro catheters or leads) are passed from the proximal end 40 to the distal end 35. By utilizing the core wall lumens 30 for any one, some or all of the aforementioned purposes, the central lumen 50 may be reserved for use by a physician as a pathway for introducing medical instruments and devices into the patient.

Method of Manufacturing the Tubular Body

Figure 12:
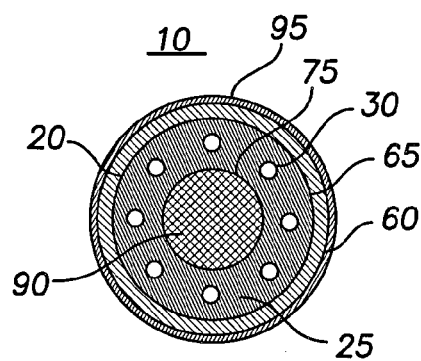
FIG. 12 is the same view depicted in FIG. 11, except a heat-shrink layer has been placed about the polymer layer.
Figure 13:
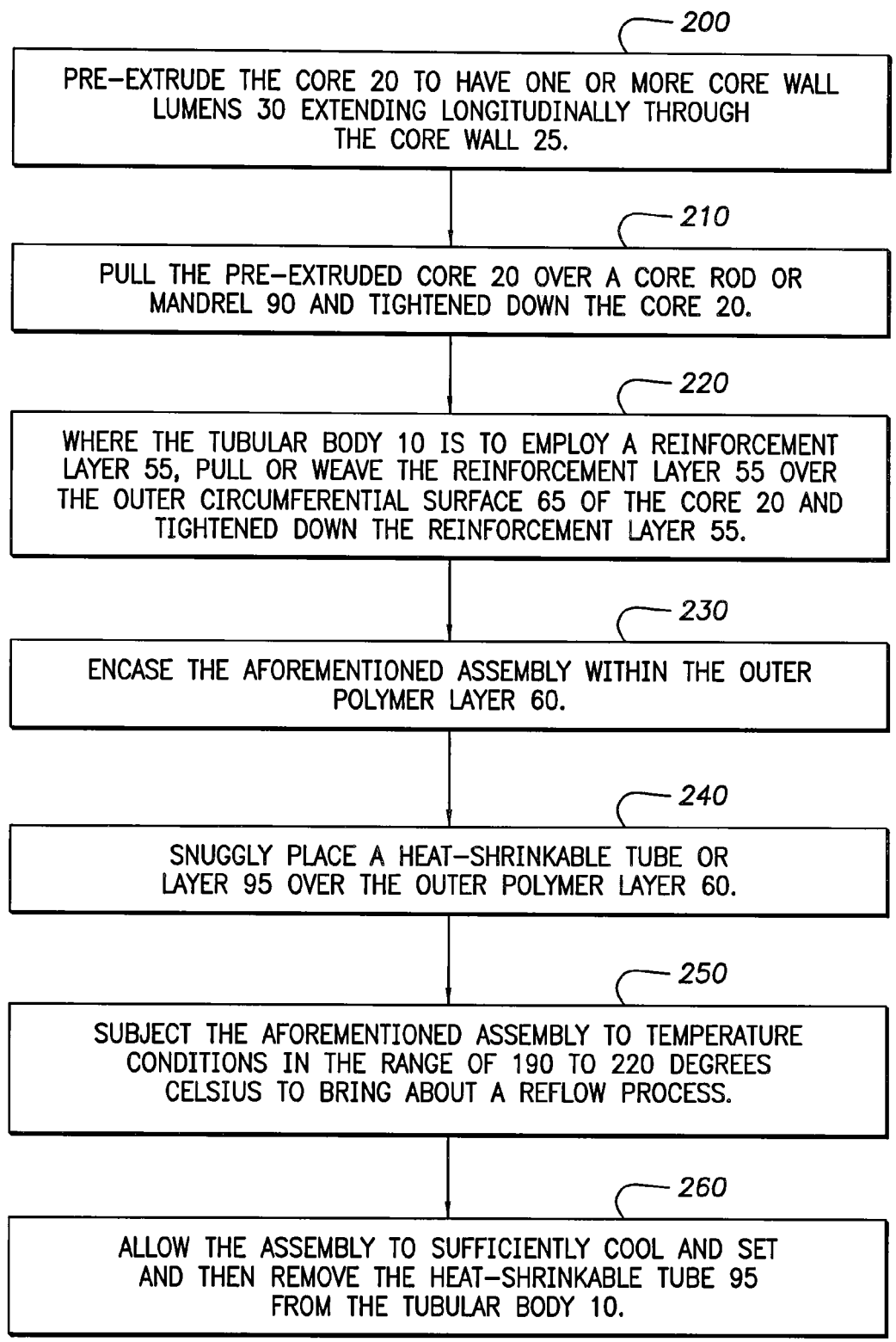
FIG. 13 is a flow chart outlining the method of manufacturing the tubular bodies illustrated in FIGS. 1A-2B.

For a discussion of a method of manufacturing the tubular body 10, reference is made to FIGS. 3-13. FIGS. 3-8 are cross-sectional elevations of the tubular body 10 at various stages of the body's manufacture, wherein the tubular body 10 employs a reinforcement layer 55 and as if taken along section line A-A in FIG. 1A. FIGS. 9-12 are cross-sectional elevations of the tubular body 10 at various stages of the body's manufacture, wherein the tubular body 10 does not employ a reinforcement layer 55 and as if taken along section line B-B in FIG. 2A. FIG. 13 is a flow chart outlining the method of manufacturing the tubular body 10 illustrated in FIGS. 1 and 2.

Figure 9:
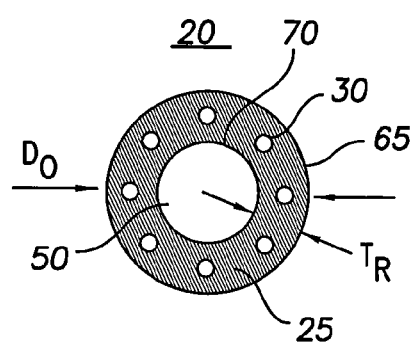
FIG. 9 is a cross-sectional elevation of a core subsequent to being extruded and prior to being combined with other components to form the tubular body, as if taken along section line B-B in FIG. 2A.

As depicted in FIGS. 3 and 9, in one embodiment, the core 20 is pre-extruded from a thermoplastic polymer [block 200]. In one embodiment, the thermoplastic polymer is PTFE. In another embodiment, the thermoplastic polymer is polyetheretherketone ("PEEK"). As the core 20 is pre-extruded, a circumferentially continuous core wall 25 is formed. The inner circumferential surface 70 of the core wall 25 defines the central lumen 50.

In one embodiment, where the tubular body 10 forms part of a catheter or sheath 15, the core 20 has an overall diameter $D_O$ of between approximately 0.03 inch and approximately 0.50 inch, and the core wall 25 has a radial thickness $T_R$ of between approximately 0.003 inch and approximately 0.030 inch. In one embodiment, the core 20 has an overall diameter $D_O$ of between approximately 0.05 inch and approximately 0.70 inch, and the core wall 25 has a radial thickness $T_R$ of between approximately 0.01 inch and approximately 0.030 inch. In one embodiment, the core 20 has an overall diameter $D_O$ of at least approximately 0.03 inch, and the core wall 25 has a radial thickness $T_R$ of at least approximately 0.003 inch. In another embodiment, where the tubular body 10 forms part of a lead 15, its core 20 and core wall 25 will be proportionately similar to those of the aforementioned catheter or sheath tubular bodies 10, except the lead tubular body 15 will have an overall diameter $D_O$ that is appropriate for a lead (e.g., pacing lead).

Figure 14:
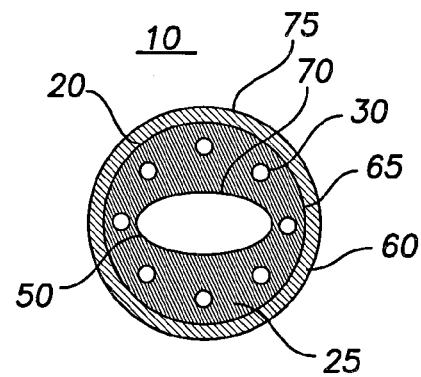
FIG. 14 is a cross-sectional elevation the tubular body as taken along section line B-B in FIG. 2A wherein the inner circumferential surface of the core wall defines an oval central lumen.

As can be understood from FIGS. 1A, 2A and 3, in one embodiment, the radial thickness $T_R$ of the core wall 25 is generally constant about the circumference of the core wall 25. However, as depicted in FIG. 14, which is a cross-sectional elevation of one embodiment of the tubular body 10 as taken along section line B-B in FIG. 2A and wherein the inner circumferential surface 70 of the core wall 25 defines an oval central lumen 50, the radial thickness $T_R$ of the core wall 25 will vary about the circumference of the core wall 25.

Figure 15:
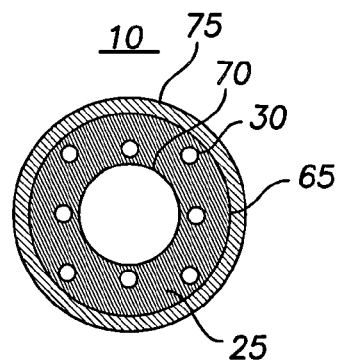
FIG. 15 is a cross-sectional elevation of one embodiment of the tubular body as taken along section line B-B in FIG. 2A and wherein the core wall lumens are evenly distributed about the circumference of the core wall, but are located at different radiuses from the longitudinal axis of the tubular body.

Regardless of whether the radial thickness $T_R$ of the core wall 25 is constant or not, the radial thickness $T_R$ of the core wall 25, in at least one location along the circumference of the core wall 25, is sufficient to receive one or more core wall lumens 30 longitudinally extending through the radial thickness $T_R$ of the core wall 25 between the outer and inner circumferential surfaces 65, 70 of the core wall 25. As depicted in FIGS. 3 and 9, in one embodiment, the core wall lumens 30 are evenly radially distributed or arrayed about the ring formed by a lateral cross-section of the core wall 25. However, in one embodiment, as shown in FIG. 15, which is a cross-sectional elevation of one embodiment of the tubular body 10 as taken along section line B-B in FIG. 2A, the core wall lumens 30 are evenly distributed about the circumference of the core wall 25, but are located at different radiuses from the longitudinal axis of the tubular body 10. Regardless of the distribution pattern of the core wall lumens 30, the core wall lumens 30 are integrally formed in the core wall 25 during the extrusion process.

In one embodiment, the core 20 is extruded from PTFE, which offers excellent thermal qualities and mechanical stability. Because of the radial thickness $T_R$ of the core walls 25 and the qualities of PTFE, the core wall lumens 30 do not collapse when the core 20 is extruded or when the core 20 is subjected to the reflow process.

In one embodiment, there will be between approximately four and approximately sixteen core wall lumens 30 extending through the radial thickness $T_R$ of the core wall 25. In other embodiments, there will be a greater or lesser number of core wall lumens 30. In one embodiment, there will be zero core wall lumens 30. In one embodiment, as previously discussed, the core wall lumens 30 are evenly radially distributed or arrayed about the ring formed by a lateral cross-section of the core wall 25, and in one embodiment, the core wall lumens 30 are not evenly distributed. In one embodiment, each core wall lumen 30 will have a diameter of between approximately 0.005 inch and approximately 0.0015 inch.

In one embodiment, to prevent the core wall lumens 30 from collapsing during the extrusion or reflow processes, the distance across a portion of the core wall 25 between the inner circumferential surface of the core wall lumen 30 and the outer circumferential surface 65 of the core 20 is at least approximately 0.0025 inch. Similarly, the distance across a portion of the core wall 25 between the inner circumferential surface of the core wall lumen 30 and the inner circumferential surface 70 of the core 20 is at least approximately 0.0025 inch. Thus, as an example, where a core wall lumen 30 has a diameter of approximately 0.005 inch, the radial thickness $T_R$ of the core wall 25 will be at least approximately 0.010 inch.

Figure 4:
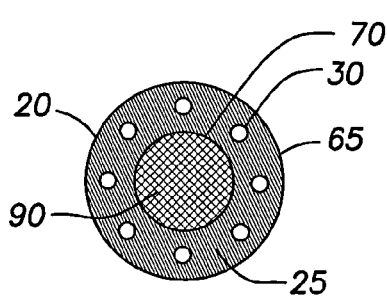
FIG. 4 is the same view depicted in FIG. 3, except the core has been placed on a mandrel.
Figure 5:
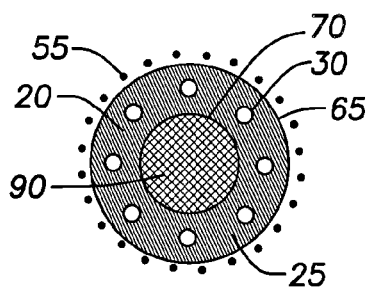
FIG. 5 is the same view depicted in FIG. 4, except a reinforcement layer has been placed about the core.
Figure 10:
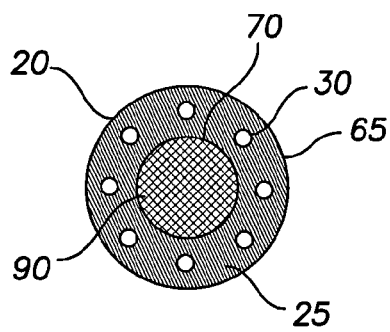
FIG. 10 is the same view depicted in FIG. 9, except the core has been placed on a mandrel.

As indicated in FIGS. 4 and 10, the pre-extruded core 20 is pulled over a core rod or mandrel 90 and tightened down [block 210]. As illustrated in FIG. 5, where a reinforcement layer 55 is utilized, the reinforcement layer (i.e., a cylindrical wire braid) 55 is pulled or woven over the outer circumferential surface 65 of the core 20 and tightened down [block 220].

Figure 6:
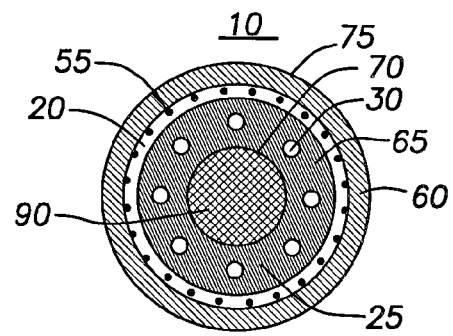
FIG. 6 is the same view depicted in FIG. 5, except a polymer layer has been placed about the core.
Figure 11:
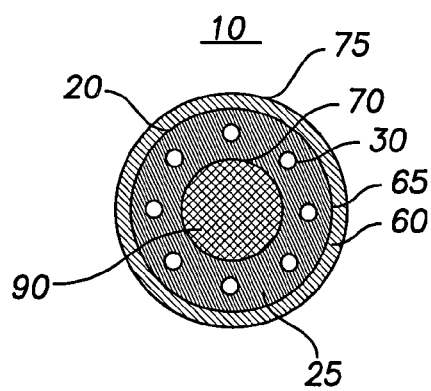
FIG. 11 is the same view depicted in FIG. 10, except a polymer layer has been placed about the core.

As shown in FIGS. 6 and 11, the entirety of the aforementioned components is then encased within the outer polymer layer 60 [block 230]. For example, in one embodiment, the outer polymer layer 60 is a pre-extruded polymer layer that is pulled over the aforementioned components and tightened down. In another embodiment, the outer polymer layer 60 is extruded over or sprayed onto the aforementioned components. In one embodiment, the outer polymer layer 60 is a polymer material such as PEBAX, polyurethane, polyethylene, nylons, silicone, etc. In one embodiment, the outer polymer layer 60 is PEBAX having a durometer value of between approximately 25 Shore D hardness to approximately 72 Shore D hardness.

Figure 7:
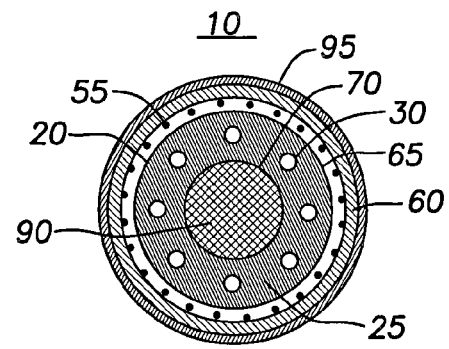
FIG. 7 is the same view depicted in FIG. 6, except a heat-shrink layer has been placed about the polymer layer.

As depicted in FIGS. 7 and 12, a heat-shrinkable tube or layer 95 is snuggly placed over the outer polymer layer 60 [block 240]. In one embodiment, the heat-shrinkable tube 95 is a polymeric material such as FEP. In one embodiment, the heat-shrinkable tube or layer 95 has a shrink temperature ranging from approximately 190 degrees Celsius to approximately 220 degrees Celsius.

Figure 8:
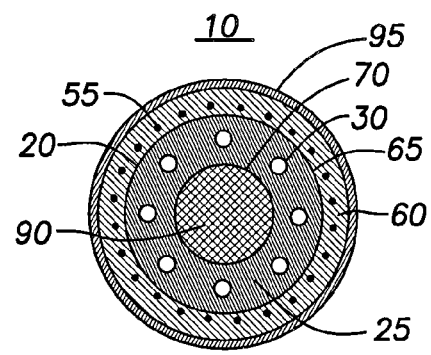
FIG. 8 is the same view depicted in FIG. 7, except the polymer layer has been reflowed to impregnate the reinforcement layer and to bond to the core.

The assemblies depicted in FIGS. 7 and 12 are subjected to the aforementioned temperature conditions to bring about the reflow process [block 250]. This causes the polymer layer 60, which, in one embodiment, is formed of PEBAX, to melt, impregnate the reinforcement layer 55 (where present), and consolidate with the outer circumferential surface 65 of the core 20. In one embodiment, the core 20 is formed of PTFE and chemically etched on the outer circumferential surface 65. Once the reflow process is complete, the assembly appears as depicted in FIG. 8 or 12. Once the newly laminated tubular body 10 has sufficiently cooled and set, the shrinkable tube 95 is removed from the tubular body 10 [block 260]. The tubular body 10 then appears as shown in FIG. 1B or 2B.

In one embodiment, the core 20 is extruded from PTFE, which, as previously mentioned, offers excellent thermal qualities and mechanical stability. The radial thickness $T_R$ of the core wall 25 is sufficiently great that the reflow process used to form the tubular body 10 does not cause the core wall lumens 30 to collapse during the extrusion or reflow processes.

PTFE cores 20 lend themselves well to both the formation of deflectable tubular bodies 10 and fixed curved tubular bodies 10. This is partly because PTFE tends to maintain its form when heated, and partly because of the radial thickness $T_R$ of the core wall 25.

In one embodiment, the polymeric material used for the core 20 has a melting or softening point that is higher than those polymeric materials used for the outer polymer layer 60 and the heat-shrinkable tube 95. In one embodiment, the polymeric materials used to form the core 20 and outer polymer layer 60 are chemically compatible such that they can be thermally bonded at the interfaces between the various polymeric materials.

In another embodiment, where the various polymeric materials are not necessarily chemically compatible such that they will thermally bond, the interfacing surfaces of the various materials will be subjected to physical or chemical surface modification to achieve reliable surface bonding. Physical surface modification includes plasma, corona, and laser surface treatments. Chemical surface modification includes chemical etching methods.

Outright chemical compatibility between the various polymeric materials or surface modification to achieve reliable surface bonding is necessary to ensure that the tubular body 10 is fully laminated during the lamination (i.e., reflow) process into an integral structure in the form of interfacial bonding by means of liquefying the outer polymer layer 60. When heat is applied, the heat-shrinkable tube 95 starts to generate varying lamination pressure, which transfers inwards the thermal energy to liquefy the outer polymer layer 60 during the lamination process.

To ensure that the outer polymer layer 60 is completely liquefied during the lamination process, the shrink temperature of the heat-shrinkable tube 95 must be higher than the softening or melting temperature of the outer polymer layer 60. The combination of the heat and pressure during lamination results in an integral tubular body 10 via polymer melt flow and interfacial bonding among all laminated components.

In one embodiment, the core wall lumens 30 form stress concentrations that extend along the length of the tubular body 10. The stress concentrations form integral split/peel lines that allow the tubular body 10 to be longitudinally split/peeled by simply laterally forcing apart opposite sides of the core wall 25. In one embodiment, to facilitate the start of a slit/split in the core wall 25, the core wall 25 is scored for a short longitudinally extending segment at the proximal end of the tubular body 10. In one embodiment, the slit/split score segment 100 longitudinally aligns with a core wall lumen 30, as depicted in FIGS. 1A-2B. In one embodiment, the scoring of the core wall 25 occurs prior to being subjected to the reflow process. In one embodiment, the scoring of the core wall 25 occurs after the reflow process. Where the core 20 is formed from PTFE, the stress concentrations caused by the core wall lumens 30 are especially effective for causing the tubular body 10 to be readily longitudinally splittable/peelable.

Once the process for laminating the tubular body into an integral unit is completed, the various functional components (i.e., deflection wires 80, conductor wires 85, etc.) are inserted into their respective core wall lumens 30. Where the core 20 is formed from a low-friction material such as PTFE, very little friction will result between a functional component and the core wall lumen 30 receiving the functional component. This increases the ease of assembly for the tubular body 10.

Figure 16:
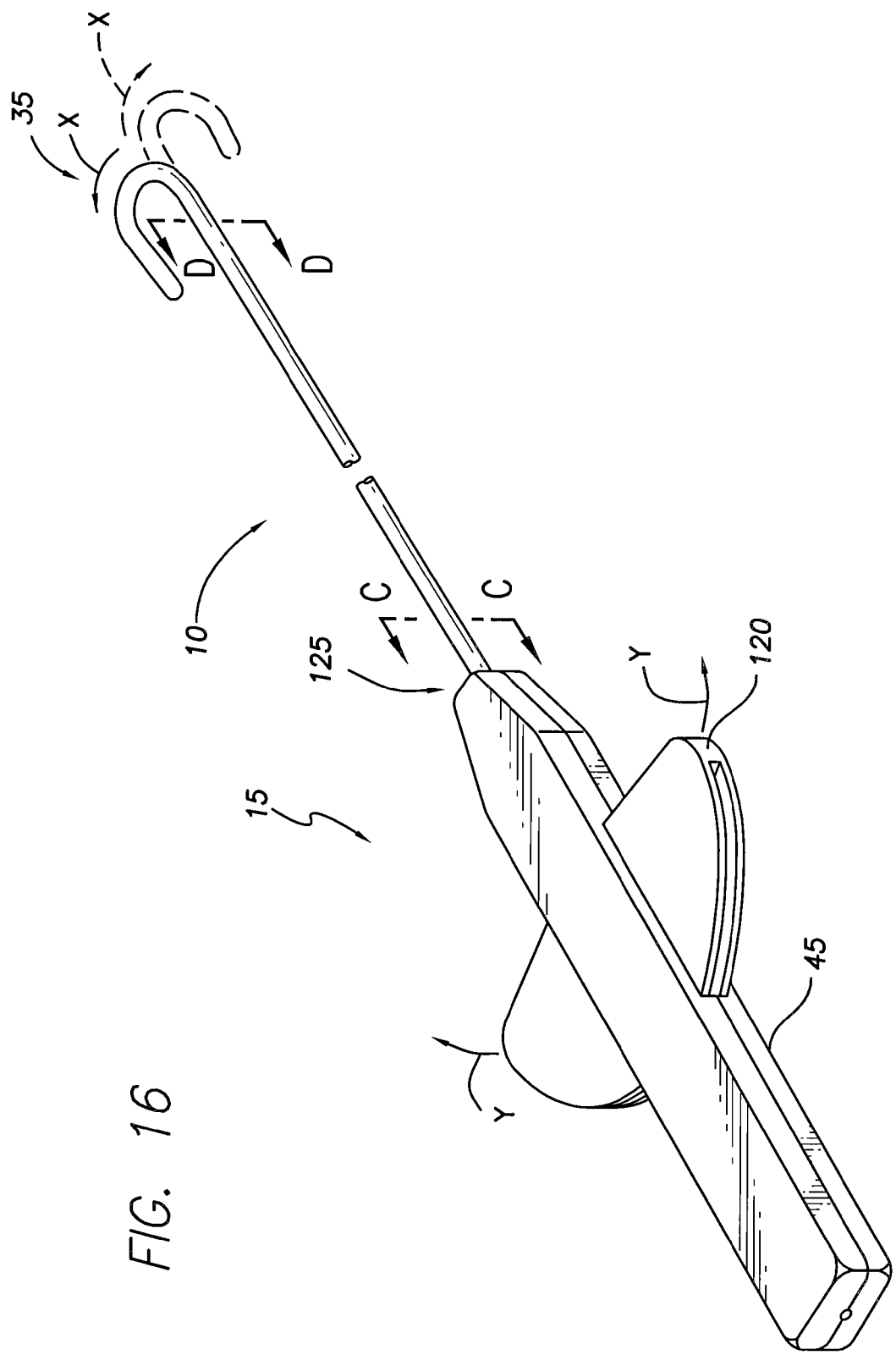
FIG. 16 is an isometric view of a deflectable catheter or sheath employing the tubular body of the subject invention.
Figure 17:
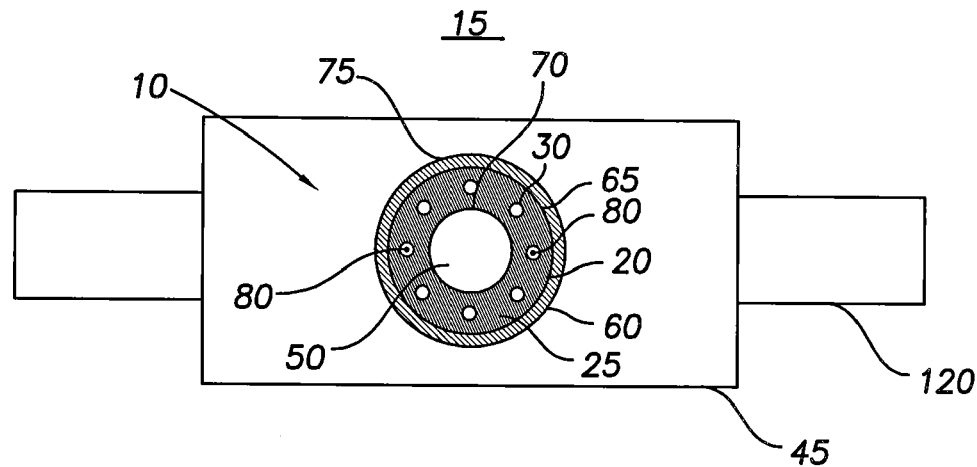
FIG. 17 is a latitudinal cross-sectional elevation taken through the tubular body near the tubular body's point of connection to the handle, as taken through section line C-C in FIG. 16 and when the core twist is not properly accounted for during assembly of the catheter or sheath.
Figure 18:
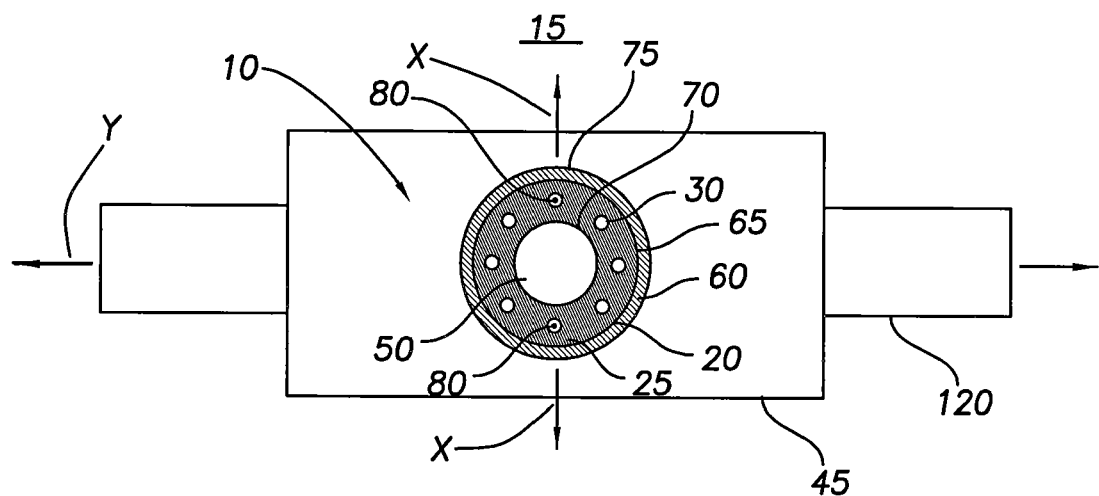
FIG. 18 is a latitudinal cross-sectional elevation taken through the tubular body near the tubular body's distal end, as taken through section line D-D in FIG. 16 and when the core twist is not properly accounted for during assembly of the catheter or sheath.
Figure 19:
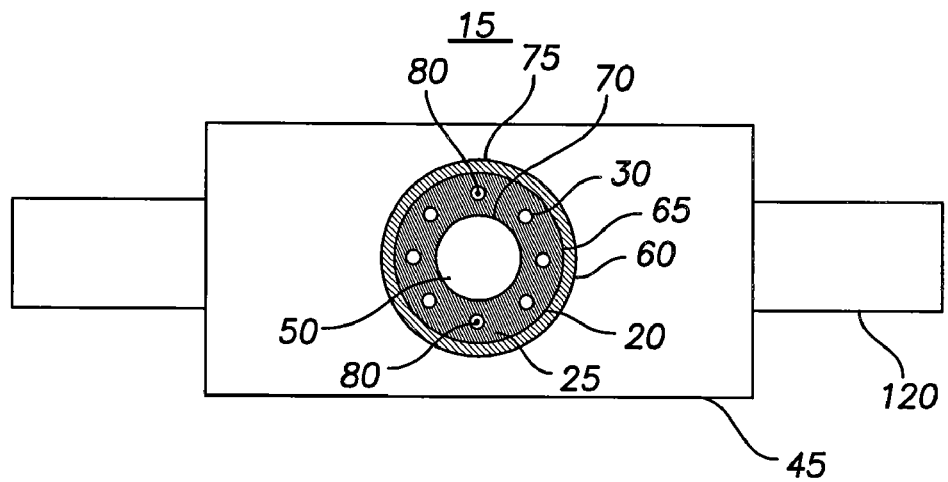
FIG. 19 is a latitudinal cross-sectional elevation taken through the tubular body near the tubular body's point of connection to the handle, as taken through section line C-C in FIG. 16 and when the core twist is properly accounted for during assembly of the catheter or sheath.
Figure 20:
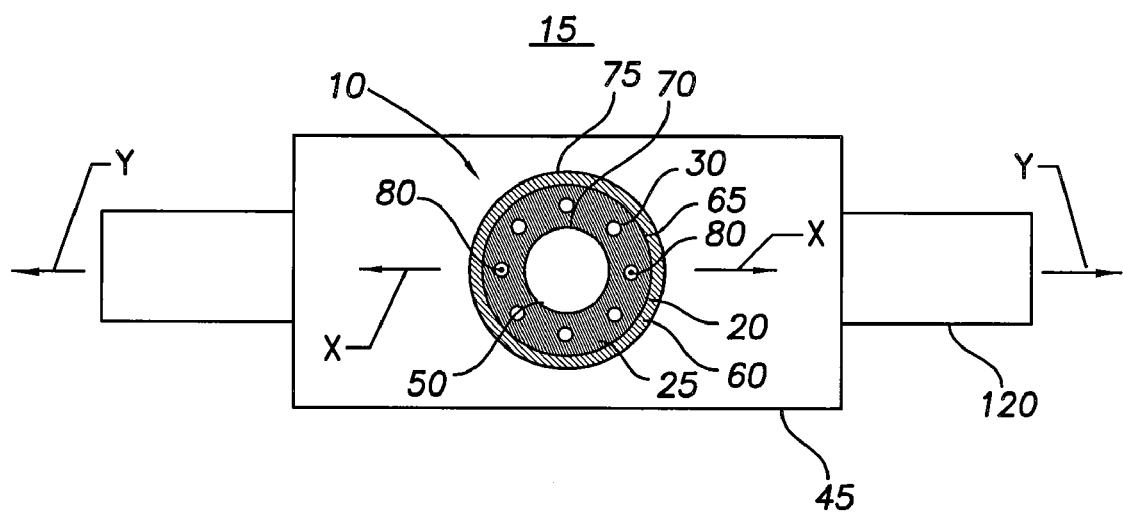
FIG. 20 is a latitudinal cross-sectional elevation taken through the tubular body near the tubular body's distal end, as taken through section line D-D in FIG. 16 and when the core twist is properly accounted for during assembly of the catheter or sheath.

In one embodiment, when the core 20 is extruded from PTFE with core wall lumens 30 and a core wall 25 having a radial thickness $T_R$ adequate to hold the core wall lumens 30, the core 20 will axially twist approximately 90 degrees every four feet the core 20 is extruded. In other embodiments, the core 20 will twist to a greater or lesser degree over the same length. The twist must be accounted for when assembling the core 20 into a deflectable tubular body 10 for a catheter or sheath 15. For a discussion regarding a method of accounting for the twist, reference is made to FIGS. 16-18. FIG. 16 is an isometric view of a deflectable catheter or sheath 15 employing the tubular body 10 of the subject invention. FIG. 17 is a latitudinal cross-sectional elevation taken through the tubular body 10 near the tubular body's point 125 of connection to the handle 45, as taken through section line C-C in FIG. 16 and when the core twist is not properly accounted for during assembly of the catheter or sheath 15. FIG. 18 is a latitudinal cross-sectional elevation taken through the tubular body 10 near the tubular body's distal end 35, as taken through section line D-D in FIG. 16 and when the core twist is not properly accounted for during assembly of the catheter or sheath 15. FIG. 19 is a latitudinal cross-sectional elevation taken through the tubular body near the tubular body's point 125 of connection to the handle 45, as taken through section line C-C in FIG. 16 and when the core twist is properly accounted for during assembly of the catheter or sheath 15. FIG. 20 is a latitudinal cross-sectional elevation taken through the tubular body 10 near the tubular body's distal end 35, as taken through section line D-D in FIG. 16 and when the core twist is properly accounted for during assembly of the catheter or sheath 15.

As can be understood from FIG. 16, the handle 45 of the catheter or sheath 15 includes an actuator 120 pivotally coupled to the rest of the handle 15. The actuator 120 is adapted to cause the deflection of the deflection wires 80 within the tubular body 10 to cause the deflection of the distal end 35 of the tubular body 10 When the core twist is properly accounted for during the assembly of the catheter or sheath 10, the actuator 120 is laterally displaceable relative to the rest of the handle 15 (as indicated by arrows Y in FIG. 16), and the distal end 35 of the tubular body 10 is also laterally displaceable (as indicated by arrows X in FIG. 16). In other words, the actuator 120 and distal end 35 of the tubular body 10 laterally displace within the same plane or within parallel planes.

In one embodiment, as previously mentioned, the core 20 twists 90 degrees in four feet of extruded length. The results of failing to account for the core twist can be understood by referring to FIGS. 17 and 18. By simply attaching the tubular body 10 to the handle 45 such that the deflection wires 80, at the point of connection 125 (see FIG. 17), reside in the same plane in which the actuator 120 displaces, the distal end 35 of the tubular body 10 will deflect in a plane (as indicated by arrows X in FIG. 18) that is perpendicular to the displacement of the actuator 120 (as indicated by arrows Y in FIG. 18). This results in a deflectable catheter or sheath 15 that is not intuitively operable for a physician.

For an understanding of the tubular body orientation relative to the handle 45 when the core twist is properly accounted for, reference is made to FIGS. 19 and 20. To properly account for the core twist, in one embodiment, the tubular body 10 is attached to the handle 45 such that the deflection wires 80, at the point of connection 125 (see FIG. 19), reside in a plane that is perpendicular to the plane in which the actuator 120 displaces. A series of pulleys and guides within the handle 45 then direct the deflection wires 80 into proper coplanar alignment with the actuator 120. As a result of this connection arrangement between the tubular body 10 and the handle 45 at the point of connection 125, the distal end 35 of the tubular body 10 will deflect in a plane (as indicated by arrows X in FIG. 20) that is coplanar with the displacement of the actuator 120 (as indicated by arrows Y in FIG. 20). This results in a deflectable catheter or sheath 15 that is intuitively operable for a physician.

Method of Peeling/Splitting a Tubular Body

The present invention, in one embodiment, is a method of peeling/splitting a tubular body 10 of a catheter, sheath or lead 15. The method comprises peeling/splitting the tubular body 10 along a lumen 30 extending longitudinally through a radial thickness $T_R$ of a wall 25 of a core 20 of the tubular body 10. In one embodiment, the peeling/splitting is started at a short score line 100, which is located at the proximal end 40 of the tubular body 10 and aligned with the lumen 30.

In one embodiment, an outer polymer layer 60 will extend about the outer circumferential surface 65 of the core 20 in a circumferentially continuous manner. The outer polymer layer 60 will be formed from two or more longitudinally extending strips of differing, but compatible, materials that extend along the length of the core 20. For example, in one embodiment, the two strips of differing materials are the same polymer material, except one strip is loaded with a radiopaque material. For an example of such an embodiment, see U.S. Provisional Patent Application 60/675,973, entitled "Splitable Tubular Body for a Catheter or Sheath," filed Apr. 28, 2005, and hereby incorporated by reference in its entirety. The longitudinally extending strips join to form the circumferentially continuous outer polymer layer 60 extending about the outer circumferential surface 65 of the core 20. Where the strips join each other, they form a boundary line that creates a line of stress concentration that can be used to peel/split the outer polymer layer 60. To allow the core 20 to be peeled/split along with the outer polymer layer 60, the tubular body 10 is formed via the reflow process such that the boundary line longitudinally aligns with the lumen 30. The coinciding lines of stress concentration formed by the aligned boundaries and the lumen allow the tubular body 10 to be readily peeled/split.

MRI Compatible Tubular Body for a Catheter or Sheath

In one embodiment, the tubular body 10 of the subject invention forms a MRI compatible catheter or sheath 15 that has both sensing and distal tip deflection capabilities. For a discussion of the MRI compatible tubular body 10, reference is made to FIGS. 2A and 2B. As can be understood from FIGS. 2A and 2B, in one embodiment, the core 20 includes a core wall 25 having a radial thickness $T_R$ that is relatively large as compared to the overall diameter $D_O$ of the core 20 and as compared to the radial thicknesses of prior art core walls. In one embodiment, the radial thickness $T_R$ of the core wall 25 is between approximately 0.003 inch and approximately 0.03 inch when the overall diameter $D_O$ of the core 20 is between approximately 0.03 inch and approximately 0.70 inch.

In one embodiment, the MRI compatible tubular body 10 is extruded from PTFE, which in combination with the relatively large radial thickness $T_R$ of the core wall 25, results in a core 20 that is sufficiently strong so as to not require a reinforcement layer 55 (as utilized in the embodiment depicted in FIGS. 1A and 1B). In one embodiment of the MRI compatible tubular body, the core 25 is sufficiently strong to only require a reinforcement layer 55 formed from non-magnetic materials. Where deflection wires 80, conductor wires 85, or other devices are present within the lumens 30 of the core wall 25, the wires 80, 85 and other devices will be formed from non-magnetic materials. For example, in one embodiment, deflection wires 80 are formed of Tungsten and conductor wires 85 are formed of copper. The strength of the MRI compatible tubular body 10 and its lack of magnetic materials allow the MRI compatible tubular body 10 to be used in MRI monitored interventional procedures. MRI monitored interventional procedures are advantageous because they facilitate greater procedural accuracy.

During an MRI monitored interventional procedure, the tubular body 10 of a MRI compatible catheter or sheath 15 is inserted into a patient via, for example, a body lumen of the patient. The displacement and operation of the MRI compatible tubular body 10 is then monitored via a MRI machine.

Balloon Equipped Tubular Body for a Catheter or Sheath

Figure 28:
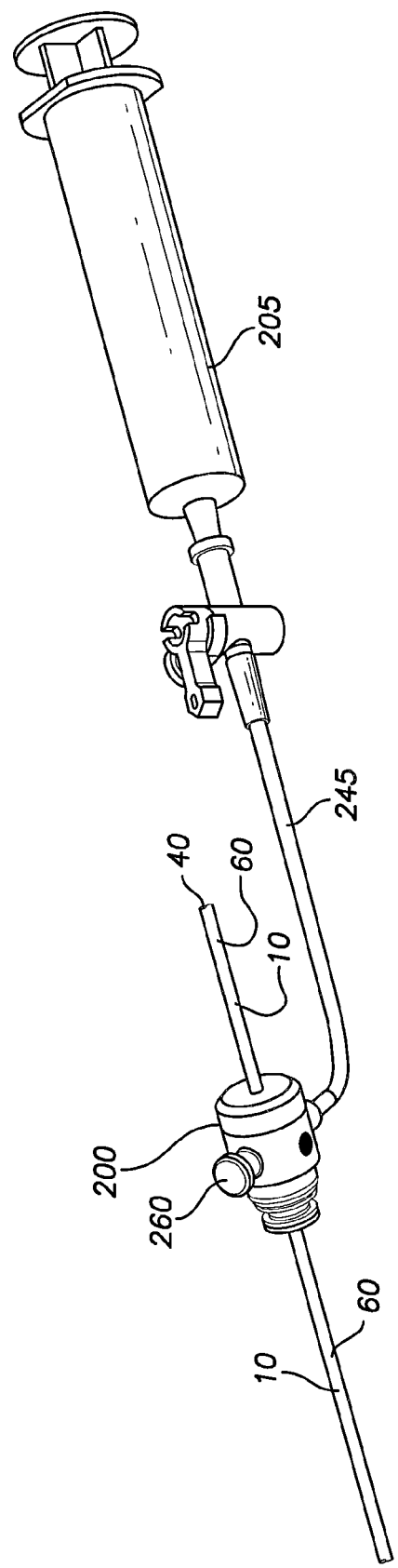
FIG. 28 is an isometric view of the proximal end of the tubular body with a fluid chamber and a syringe.
Figure 29:
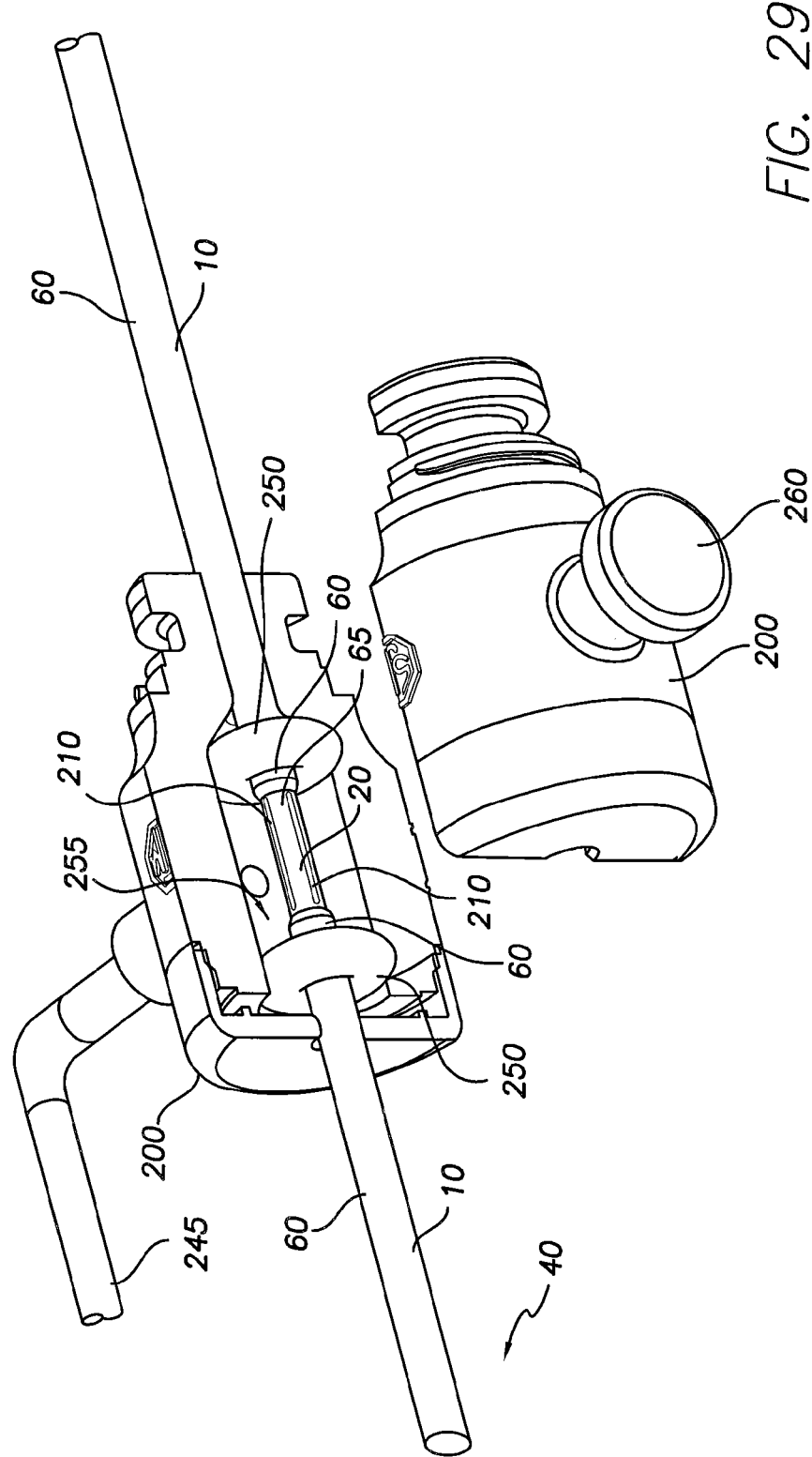
FIG. 29 is an enlarged view of the fluid chamber valve split in half to show the configuration of the tubular body within the fluid chamber.

In one embodiment, the core 20 of the subject invention is used to form a balloon equipped tubular body 10 for a catheter or sheath 15. For a discussion regarding such a tubular body 10, reference is made to FIGS. 21-29. FIGS. 21-27 are isometric views of the distal end 35 of the tubular body 10 at various stages of its assembly process. FIG. 28 is an isometric view of the proximal end 40 of the tubular body 10 with a fluid chamber 200 and a syringe 205. FIG. 29 is an enlarged view of the fluid chamber 200 split in half to show the configuration of the tubular body 10 within the fluid chamber 200.

Figure 21:
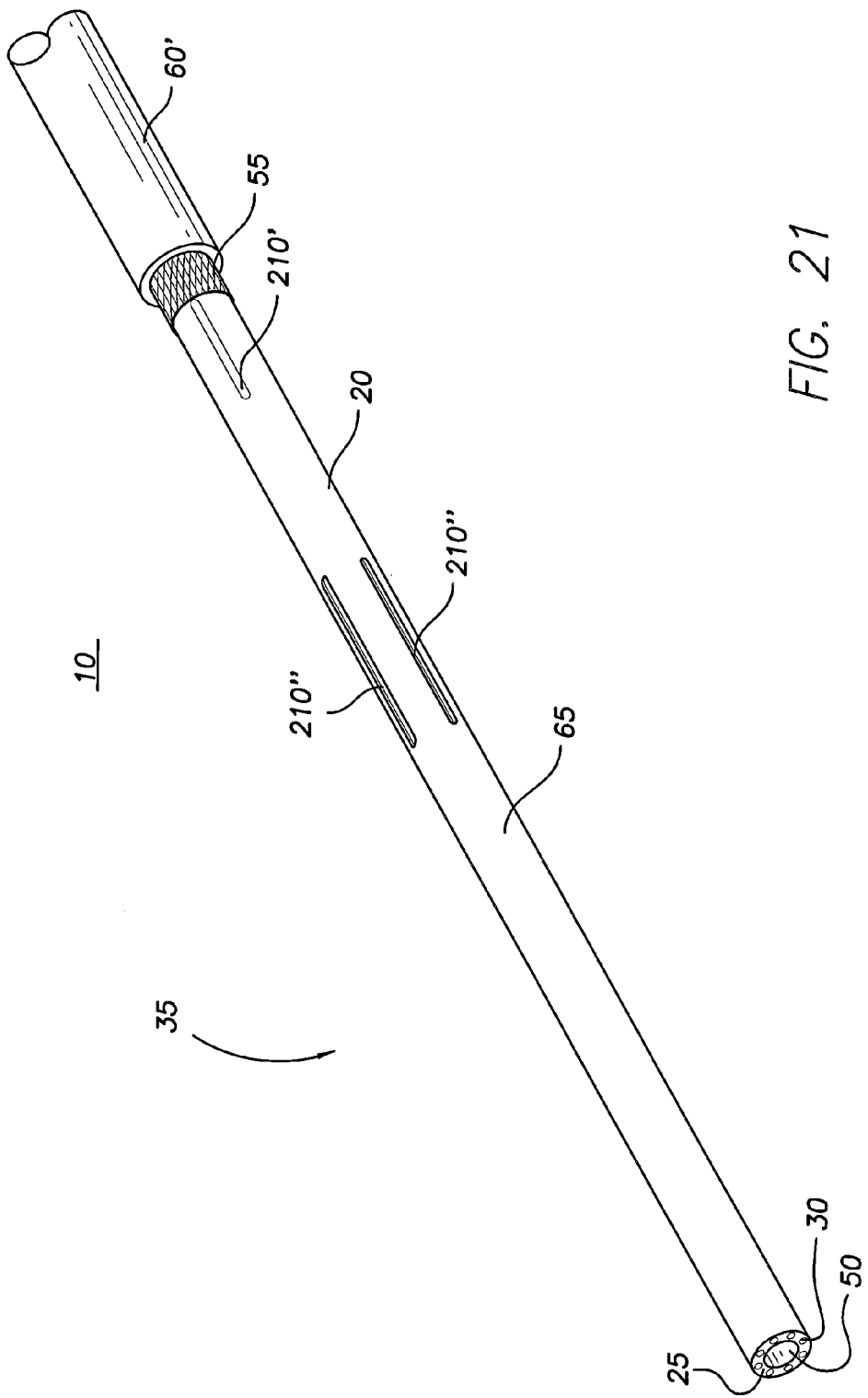
FIGS. 21-27 are isometric views of the distal end of the tubular body at various stages of its assembly process.

As indicated in FIG. 21, a first section of an outer polymer layer 60' has been reflowed about an extruded polymer core 20 having a central lumen 50 and a plurality of core wall lumens 30 longitudinally extending through the radial thickness $T_R$ of the core wall 25. In one embodiment, as depicted in FIG. 21, a braided reinforcement layer 55 will extend about the outer circumferential surface 65 of the core 20 and will be impregnated by the first section of an outer polymer layer 60'. In one embodiment, the tubular body 10 will not have a braided reinforcement layer 55. In one embodiment, the core 20 will be extruded from PTFE and the outer polymer layer will be PEBAX.

As depicted in FIG. 21, the first section of an outer polymer layer 60' and reinforcement layer 55 (where present) terminate short of the extreme distal end 35 of the tubular body 10. A proximal pair or group of slots 210' and a distal pair or group of slots 210" extend longitudinally along the outer circumferential surface 65 of the core 20. Each slot 210 extends into the core wall 25 to a core wall lumen 30 from the outer circumferential surface 65 of the core 20. In one embodiment, the slots 210 are cut via a mechanical cutting device such as a knife, saw, etc. In one embodiment, the slots 210 are cut via a laser. The proximal pair or group of slots 210' provide access to core wall lumens 30 that receive deflection wires 80. The distal pair of group of slots 210" provide access to core wall lumens 30 that transmit a fluid from the syringe 205 (see FIG. 28) to a balloon near the distal end 35 of the tubular body 10 as discussed below.

Figure 22:
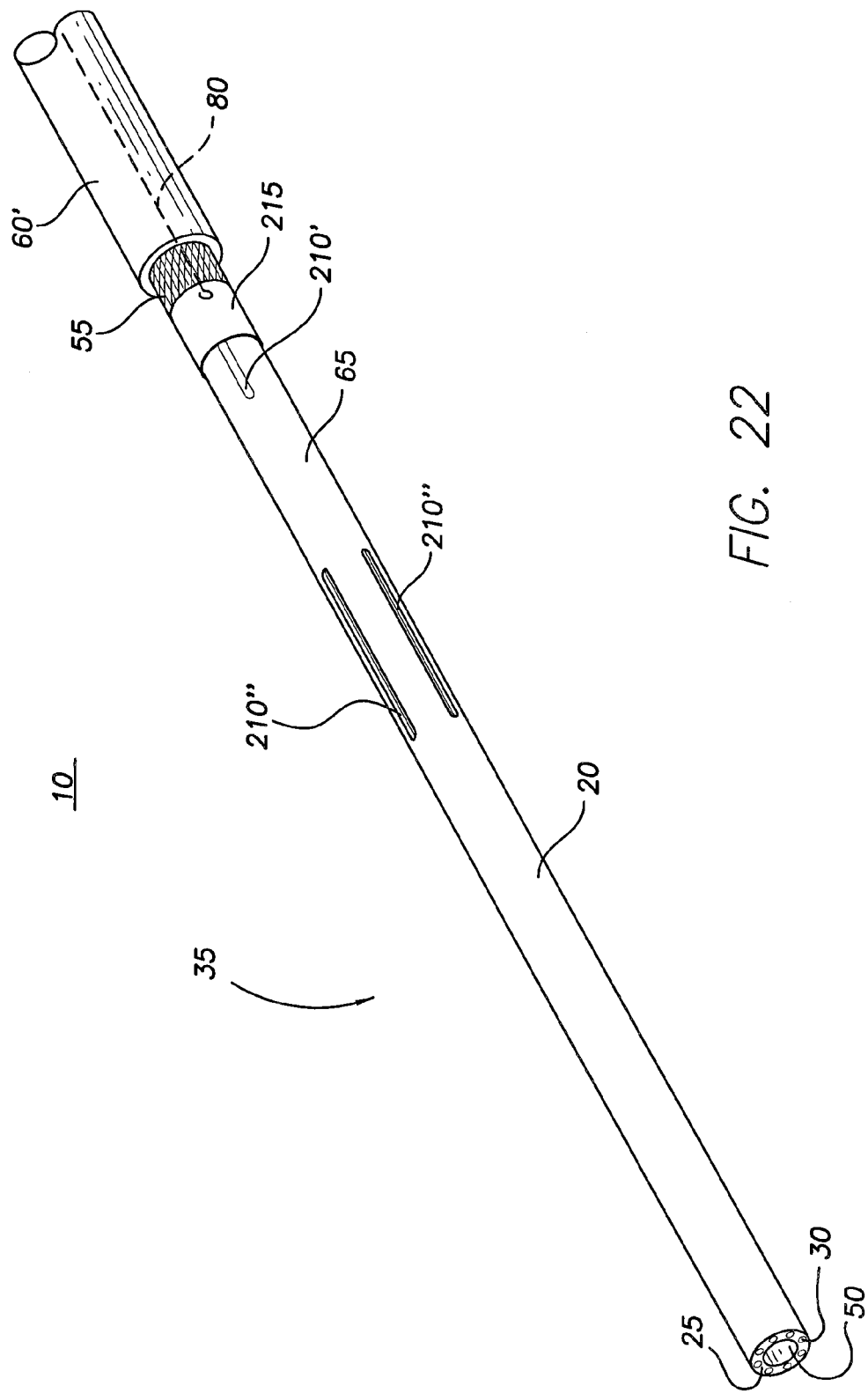

As shown in FIG. 22, a first deflection wire anchor member, collar or ring 215 has been placed over the outer circumferential surface 65 of the core 20. One or more deflection wires 80 are coupled to the first anchor member 215 via welding, mechanical, or other coupling methods. As can be understood from FIG. 22, each deflection wire 80 (shown in phantom line) has been inserted down through a proximal slot 210' and into the core wall lumen 30 accessed by the proximal slot 210'. Each deflection wire 80 extends through its respective lumen 30 to the actuation handle 45.

Figure 23:
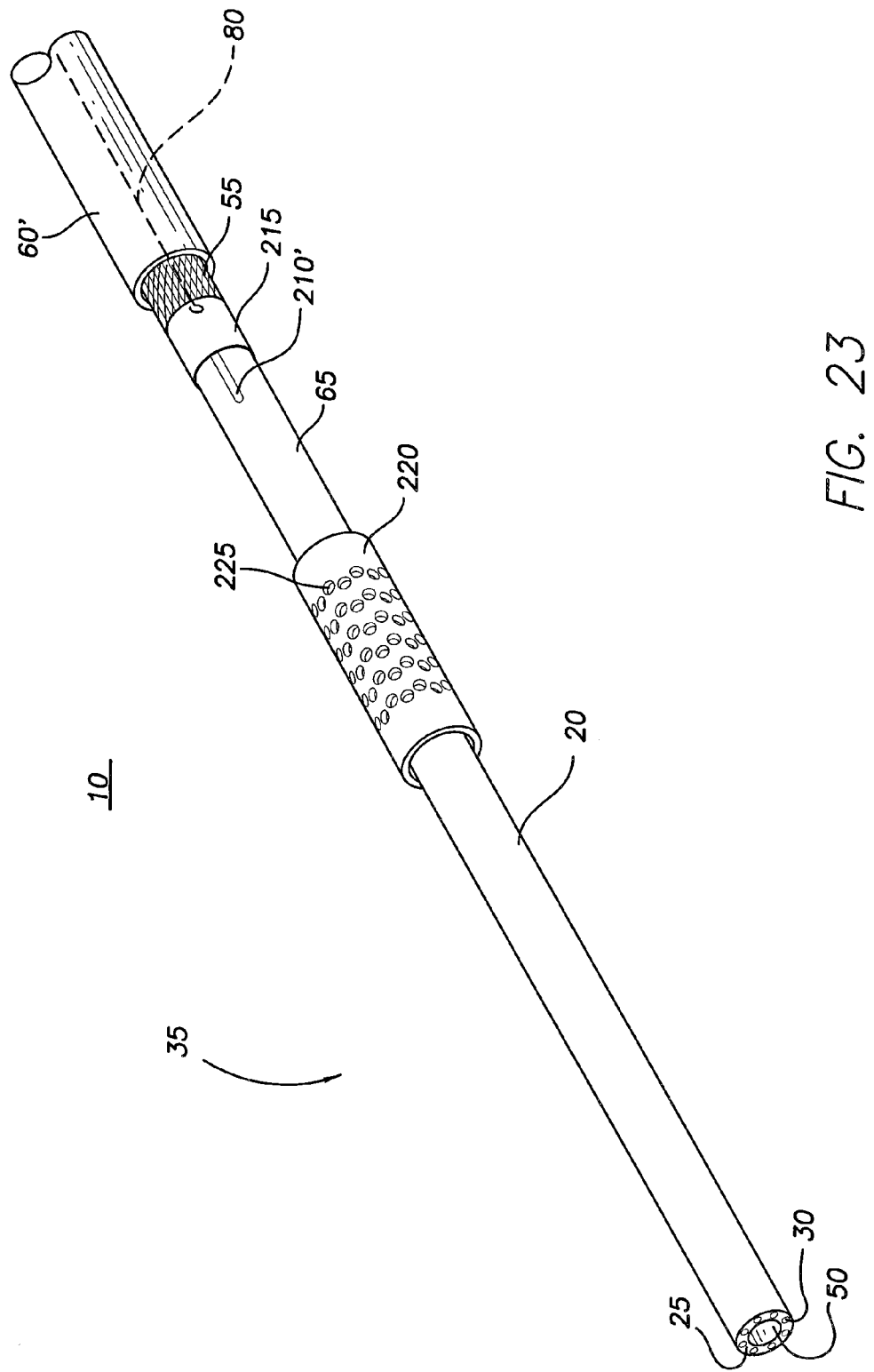

As depicted in FIG. 23, a heat shrink material 220 having a plurality of pores, perforations or holes 225 is placed about the outer circumferential surface 65 of the core 20 over the distal slots 210". The heat shrink material 220, which is FEP in one embodiment, is heat shrunk about the core 20 such that the heat shrink material 220 tightly conforms to the outer circumferential surface 65 of the core 20 and a plurality of holes 225 align with each distal slot 210". In one embodiment, the diameter of each hole 225 is approximately the same as the width of a distal slot 210". The heat shrink material 220 provides a uniform base over which a resilient elastomeric material 230 (e.g., polyisoprene, silicone, chronoprene, etc.) can be laid to form a balloon 235, as depicted in FIG. 24.

Figure 24:
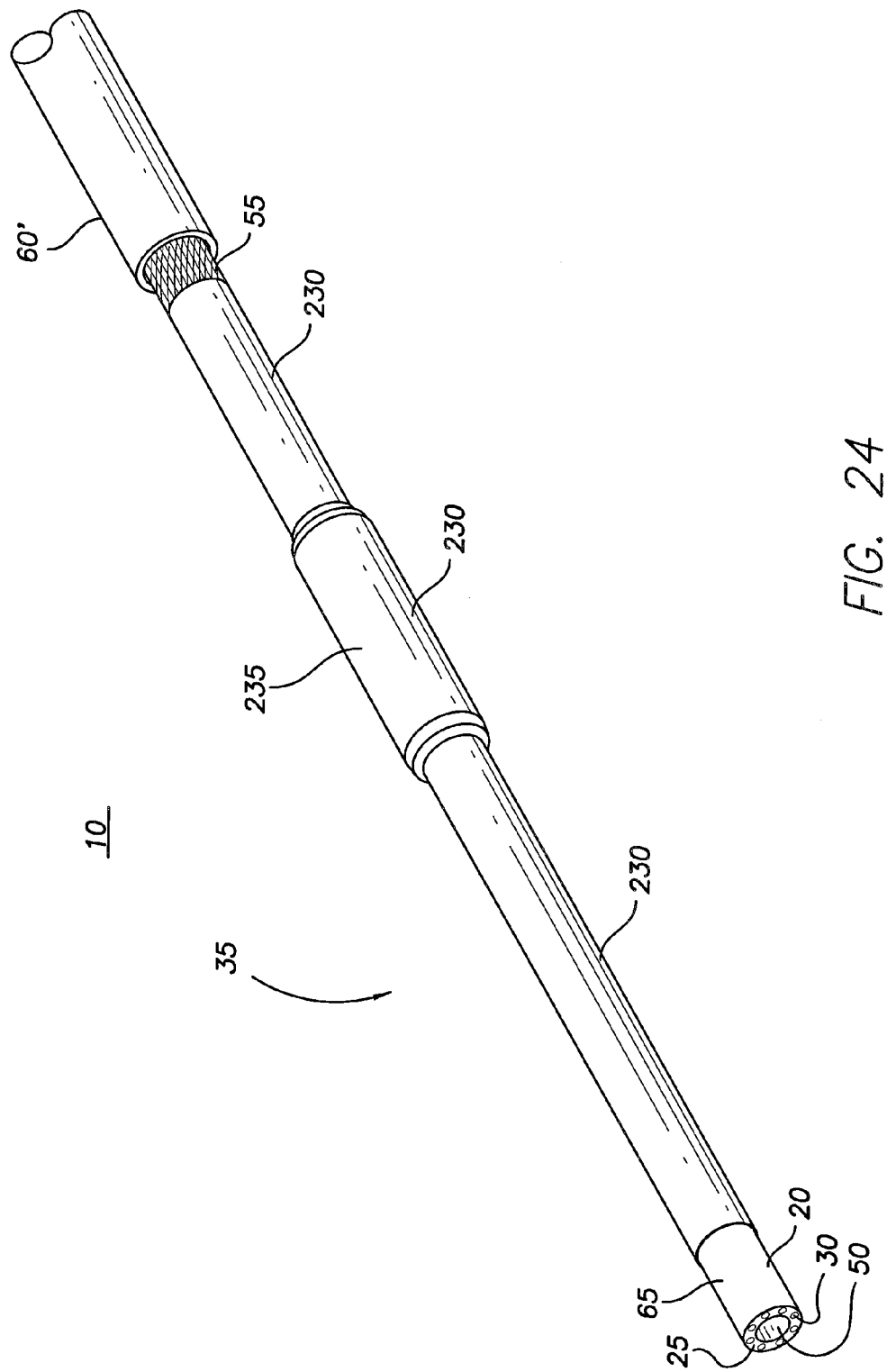
Figure 25:
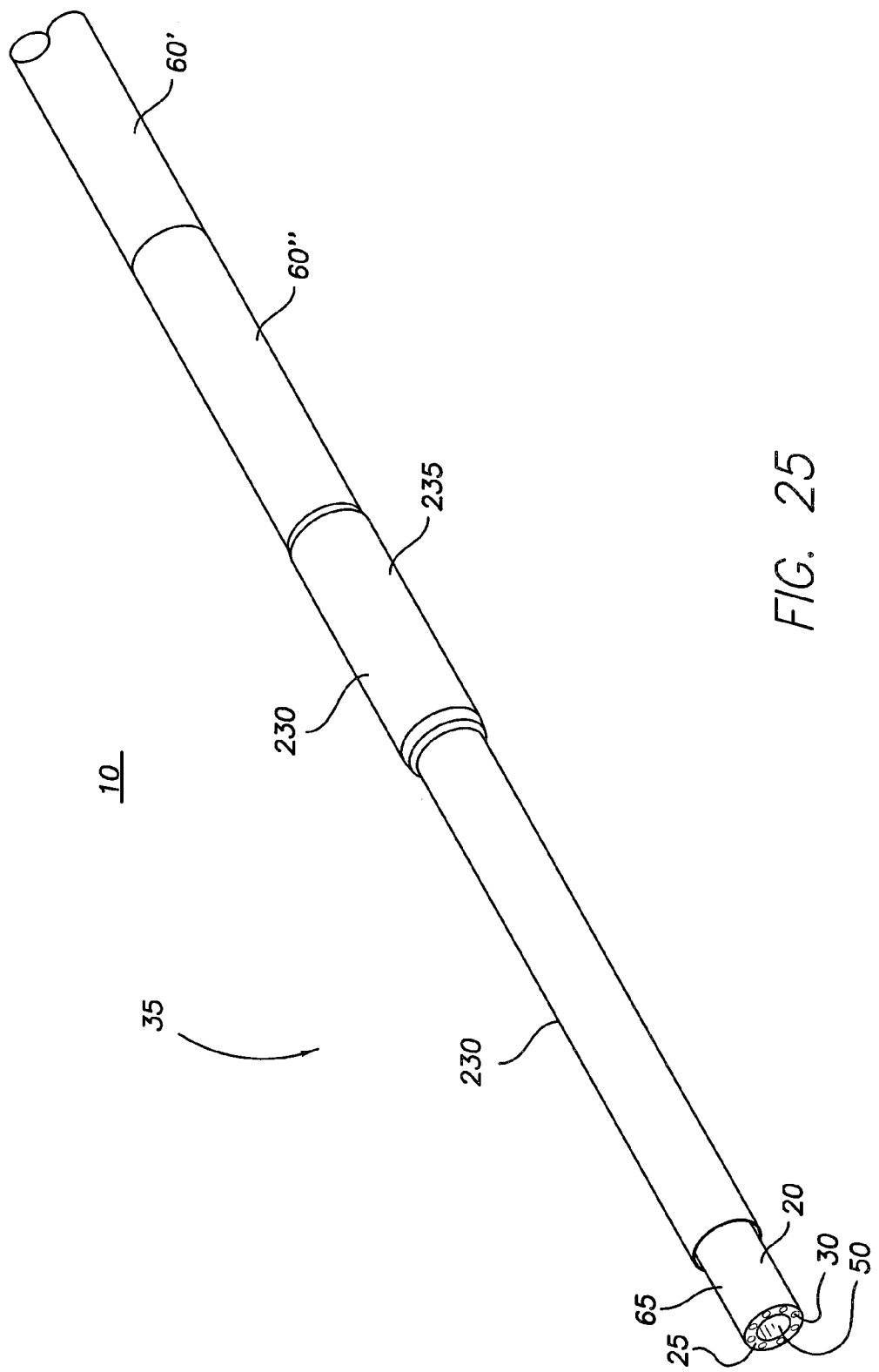

As shown in FIG. 24, in one embodiment, the elastomeric material 230 circumferentially encompasses the core 20, shrink wrap material 220, and first anchor member 215 from a point near the extreme distal end 35 of the tubular body 10 to the proximal edge of the anchor member 215 or distal edge of the reinforcement layer 55. As illustrated in FIG. 25, a second section of an outer polymer layer 60" is reflowed about the elastomeric material 230 between the proximal end of the balloon 235 and a distal end of the first section of an outer polymer layer 60'. The second section of an outer polymer layer 60" bonds to the outer circumferential surface of the elastomeric material 230 and impregnates the exposed distal end of the reinforcement layer 55 (where present) and bonds to the exposed portion of the core 20 immediately distal the proximal end of the first section of an outer polymer layer 60'. As a result, the second section of an outer polymer layer 60" bonds the proximal end of the elastomeric material 230 to the core 20 and defines the proximal edge of the balloon 235. In one embodiment, the second section of an outer polymer layer 60" is PEBAX. In one embodiment the second section of an outer polymer layer 60" has a higher durometer value than the first section of an outer polymer layer 60', which tends to force the distal end 35 of the tubular body 10 to bend at the location of the first section of an outer polymer layer 60' as opposed to bending at the location of the second section of an outer polymer layer 60".

Figure 26:
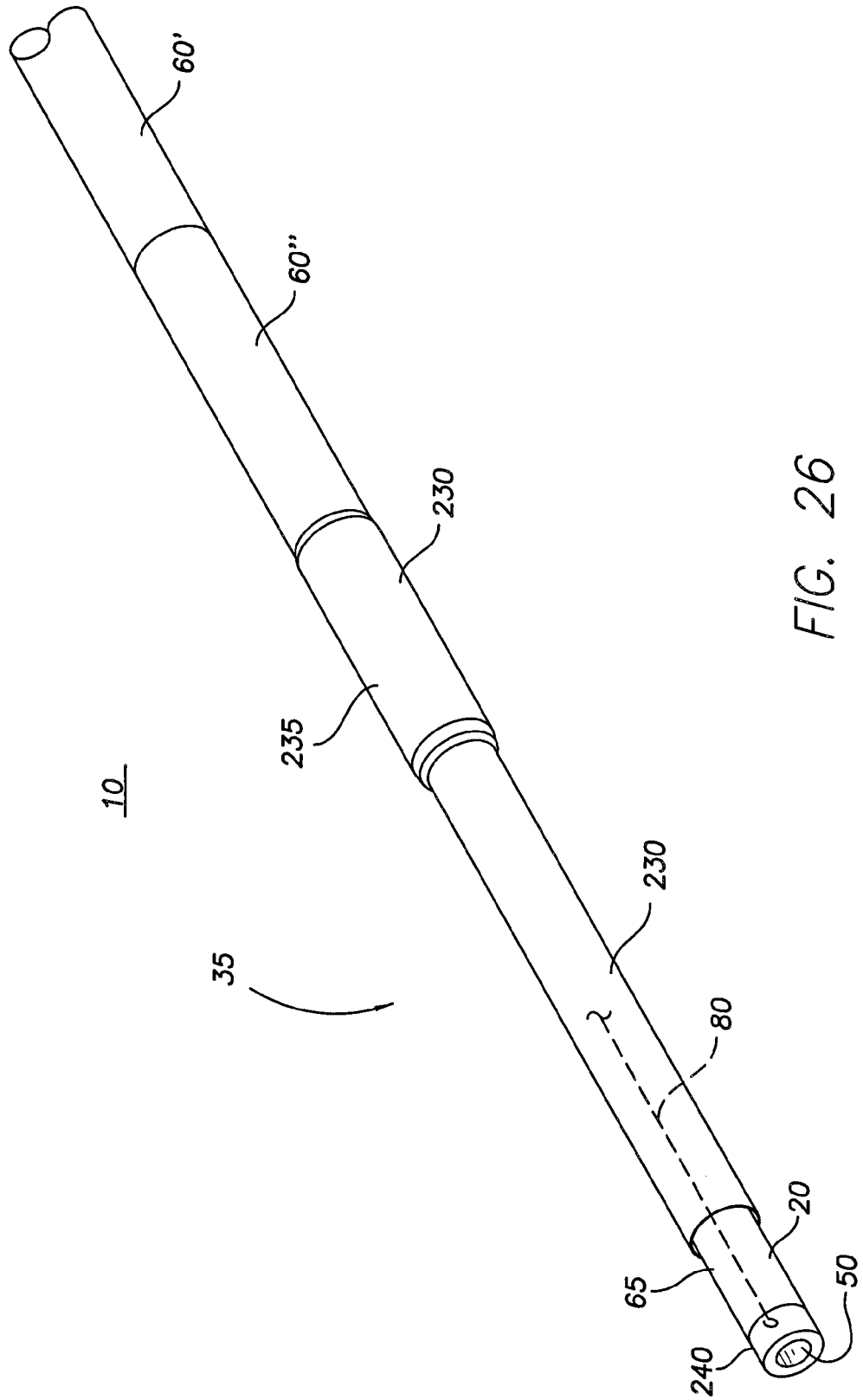

As illustrated in FIG. 26, a second deflection wire anchor member, collar or ring 240 has been placed over the extreme distal tip of the core 20, one or more deflection wires 80 are coupled to the second anchor member 215 via welding, mechanical, or other coupling methods. As can be understood from FIG. 26, each deflection wire 80 (shown in phantom line) has been inserted down through a distal opening of a core wall lumen 30 and through the core wall lumen 30 to the actuation handle 45.

Figure 27:
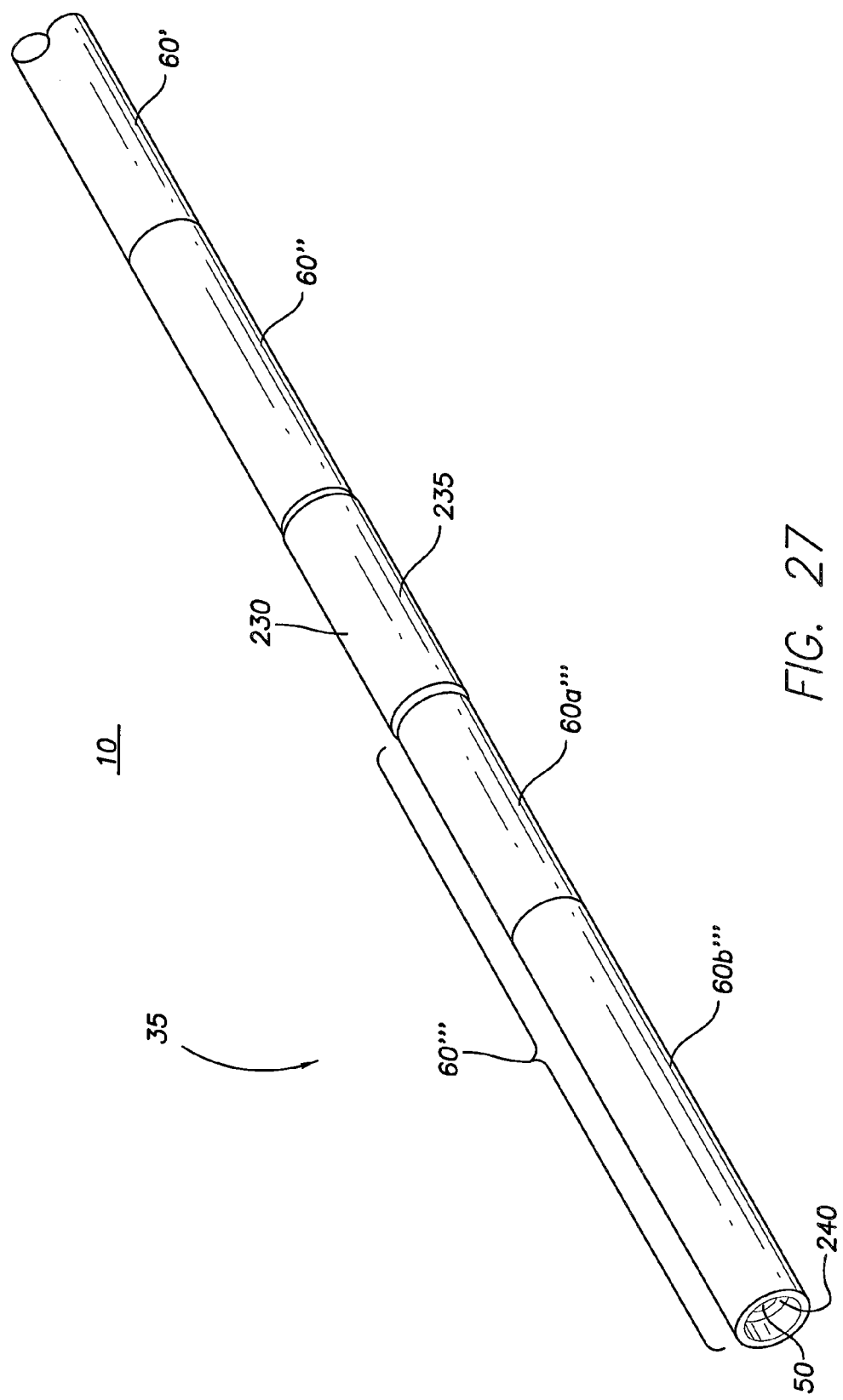

As shown in FIG. 27, in one embodiment, a third section of an outer polymer layer 60''' is reflowed about the elastomeric material 230 from a point just distal the extreme distal end 35 of the core 20 to a distal edge of the balloon 235. The third section of an outer polymer layer 60''' bonds to the outer circumferential surface of the elastomeric material 230. As a result, the third section of an outer polymer layer 60''' bonds the distal end of the elastomeric material 230 to the core 20 and defines the distal edge of the balloon 235. In one embodiment, the third section of an outer polymer layer 60''' is PEBAX. In one embodiment the third section of an outer polymer layer 60" is divided into a proximal and distal sections 60a''', 60b'''. In one embodiment, the proximal section of the third section of the outer polymer layer 60a''' has a higher durometer value than the distal section of the third section of an outer polymer layer 60b'''. This difference in durometer tends to force the distal end 35 of the tubular body 10 to bend at the location of the distal section of the third section of an outer polymer layer 60b''' as opposed to bending at the location of the proximal section of the third section of an outer polymer layer 60a'''.

As shown in FIG. 28, in one embodiment, the proximal end 40 of the tubular body 10 extends through a fluid chamber 200 and a syringe 205 is in fluid communication with a port in the fluid chamber 200 via a tube 245. The syringe 205 is used to inject a fluid into the fluid chamber 200. The injected fluid travels along one or more core wall lumens 30, through the distal slots 210" (see FIG. 21), through the holes 225 in the heat shrink material 220 (see FIG. 23), and into the balloon 230 (see FIG. 27) to cause the balloon to inflate. Withdrawing fluid back into the syringe 205 causes the balloon to deflate.

As illustrated in FIG. 29, the tubular body 10 extending proximally and distally from the fluid chamber 200 has the outer polymer layer 60 circumferentially extending about the core 20. However, inside the fluid chamber 200 and between distal and proximal o-rings 250 located within the fluid chamber 200, the outer polymer layer 60 does not extend about the core 20. As shown in FIG. 29, the tubular body 10 extends through the o-rings 250. Just inwardly of each o-ring 250 the tubular body 10 transitions from a configuration having an outer polymer layer 60 reflowed about the core 20 to a bare core 20 having slots 210 that pass through outer circumference 65 of the core 20 to place the interior volume 255 of the fluid chamber 200 into fluid communication with the core wall lumens 30 that lead to the balloon 235 shown in FIG. 27. Like the slots 210 previously discussed in reference to FIGS. 21-27, the slots 210 located within the fluid chamber 200 are formed via mechanical or laser cutting methods As can be understood from FIGS. 28 and 29, to inflate the balloon 235, a fluid is injected from the syringe 205 and into the fluid chamber 200 via the tube 245, which opens into the interior volume 255 of the fluid chamber 200. The fluid passes through the slots 210 in the core 20 and into the lumens 30 leading to the slots 210" beneath the shrink fit material 220 (see FIGS. 22 and 23). The fluid passes through the holes 225 in the shrink fit material 220 and into the balloon 235 (see FIG. 27) to cause the balloon 235 to inflate. To deflate the balloon 235, the syringe 205 draws the fluid back to itself along the same route.

As indicated in FIGS. 28 and 29, in one embodiment, the fluid chamber 200 includes a pressure relief valve 260. The valve 260 is preset to open or provide pressure relief at an inflation pressure corresponding to a specific diameter of the balloon 235. During a medical procedure, the balloon 235 is inflated to occlude a body lumen (e.g., vein, artery, etc.). To preserve the integrity of the body lumen, the balloon 235 should not be inflated beyond a certain safe diameter. The pressure relief valve 260 is preset to open at a critical pressure, which is when the inflation pressure is such that the balloon 235 will begin to exceed said certain safe diameter. By opening at the critical pressure, the pressure relief valve 260 prevents the balloon 235 from excessively inflating and damaging the body lumen. When the inflation pressure drops below the critical pressure, the pressure relief valve 260 automatically reseals until the inflation pressure again begins to exceed the critical pressure.

Method of Using a Catheter, Sheath or Lead Employing the Tubular Body of the Subject Invention In use, a puncture is made with a thin walled needle through the skin and into a blood vessel. A guidewire is then placed through the needle into the blood vessel and the needle is withdrawn. An intravascular introducer is advanced over the guidewire into the lumen of the blood vessel. The tubular body 10 is inserted into the introducer and manipulated so it travels along the blood vessel to the point of treatment (e.g., a chamber in the heart). In one embodiment, one or more of the core wall lumens 30 contain a radiopaque marker, and the travel and positioning of the tubular body 10 within the patient is monitored via X-ray fluoroscopy. In one embodiment, the tubular body 10 is MRI compatible, and the travel and positioning of the tubular body 10 within the patient is monitored via MRI.

In one embodiment, the tubular body 10 is manipulated/deflected at its distal end 35 by causing the deflection wires 80 to displace within their respective core wall lumens 30. A medical diagnosis is made or a medical treatment is delivered via electrodes at the distal end 35 that are electrically coupled to conductor wires 85 located within core wall lumens 30. Fluids are injected into or removed from the patient via core wall lumens 30 that are coupled to a fluid displacing mechanism. Micro-catheters or leads are delivered to the treatment site via core wall lumens 30.

Because the central lumen 50 is free of deflection and conductor wires 80, 85, fluid conveying conduits, and other obstructions, a medical device (e.g., a pacemaker lead) is easily inserted through the central lumen 50 of the tubular body 10 to the treatment site. Once the device is positioned and implanted within the patient, the tubular body 10 will be removed. However, to clear the pacemaker lead, the tubular body 10 will need to be split/peeled along a stress concentration formed by a core wall lumen 30 that extends along the length of the tubular body 10. Because PTFE is readily splittable/peelable along the stress concentration formed by the core wall lumen 30, the tubular body 10 splits/peels as opposed sides of the tubular body 10 force apart. In one embodiment, the split will be started via a short score segment 100 at the proximal end of the tubular body 100. Once the tubular body 10 has been split/peeled, the pacemaker lead can be cleared and the tubular body 10 can be removed from the patient without displacing the pacemaker lead.

Large Diameter Tubular Body for a Catheter or Sheath

In one embodiment, the core 20 of the subject invention illustrated in FIGS. 1A-2B is used to form a large diameter tubular body 10 for a catheter or sheath 15 wherein the tubular body 10 has a deflectable distal end 35. Such catheters or sheaths 15 are used to conduct invasive surgical procedures such as a mini-thoracotomy. In one embodiment, the tubular body 10 has a diameter of approximately 12 millimeters. In the past, a tubular body 10 with such a large diameter was not capable of being deflected at its distal end 35. However, the core 20 of the subject invention, in one embodiment, facilitates the construction of a large diameter tubular body 10 that is deflectable at its distal end 35. In one embodiment, the large diameter tubular body 10 has the ability to deflect approximately 90 degrees at the distal end 35 of the tubular body 10. In other embodiments, other ranges of deflection are possible.

For a discussion of such a tubular body 10, reference is made to FIG. 30, which is a longitudinal cross-sectional elevation of the distal end 35 of a large diameter tubular body 10 for a catheter or sheath 15. As shown in FIG. 30, the tubular body 10 includes a core 20, a cylindrical uniplanar spring 300, an elastomeric tube 305, an end ring or cap 310, a pair of deflection wires 80, a pair of conductor wires 85, and an outer polymer layer or tube 60.

Figure 32:
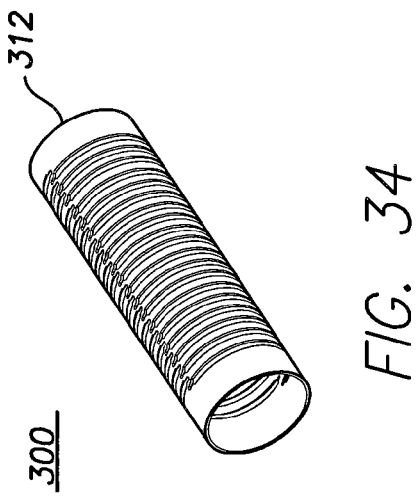
FIG. 32 is a latitudinal cross-sectional elevation of the core, as taken along section line E-E in FIG. 31.

As depicted in FIGS. 31 and 32, which are, respectively, a longitudinal cross-sectional elevation of the core 20 shown in FIG. 30 and a latitudinal cross-sectional elevation of the core 20 as taken along section line E-E in FIG. 31, the core 20 includes a core wall 25 that defines a central lumen 50 and has a plurality of core wall lumens 30 extending longitudinally through a radial thickness $T_R$ of the core wall 25. The core 20 also includes a stepped distal end 35 defined by a first outer diameter $D_O$ and a second or reduced outer diameter $D_R$ that is smaller than, and distal from, the first outer diameter $D_O$. In one embodiment, the first outer diameter $D_O$ is between approximately 0.1 inch and approximately 0.7 inch while the second or reduced outer diameter $D_R$ is between approximately 0.08 inch and approximately 0.068 inch. In one embodiment, the radial thickness $T_R$ of the core wall 25 is between approximately 0.007 inch and approximately 0.02 inch.

As shown in FIG. 30, the cylindrical uniplanar spring 300 is received about the second or reduced outer diameter $D_R$. The proximal edge 312 of the spring 300 abuts against a rim 315 defined by the change in diameter between the first and second outer diameters $D_O$, $D_R$ (see FIGS. 31 and 32).

As illustrated in FIGS. 31 and 32, in one embodiment, the radially outermost point on the circumference of each core wall lumen 30 intersects or coincides with the outer circumferential surface 315 defined by the second or reduced outer diameter $D_R$ of the core 20. As a result and as shown in FIG. 30, the deflection wires 80 exit the core wall lumens 30 and extend distally to the end ring 310 adjacent to the inner circumferential surface of the cylindrical uniplanar spring 300.

Figure 34:
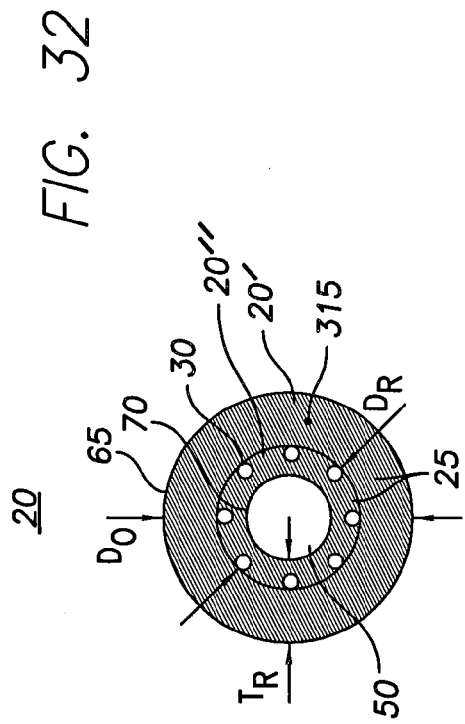
FIG. 34 is an isometric view of one embodiment of the uniplanar spring.
Figure 33:
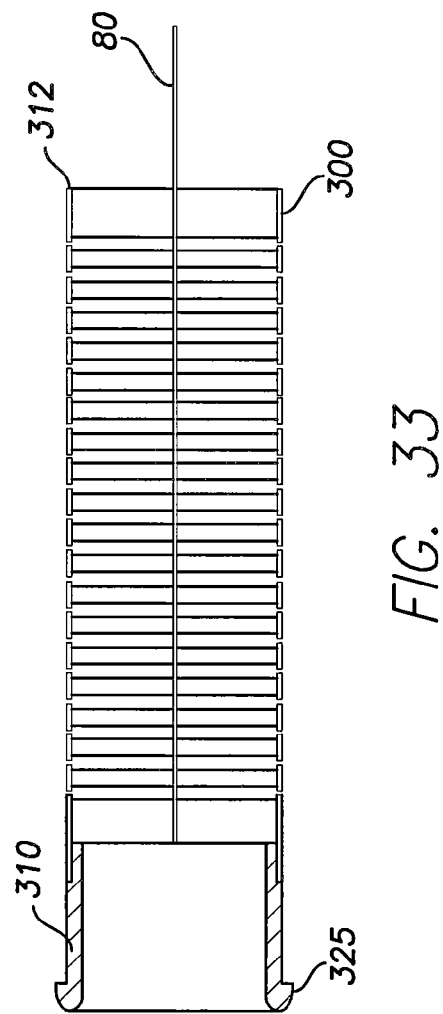
FIG. 33 is a longitudinal cross-sectional elevation of the uniplanar spring shown in FIG. 30.

As depicted in FIG. 33, which is a longitudinal cross-sectional elevation of the uniplanar spring 300 shown in FIG. 30, the distal end of each deflection wire 80 is coupled (e.g., welded) to the distal end of the spring 300 and/or to the end ring 310. When a deflection wire 80 is pulled proximally, the deflection wire 80 causes the spring to deflect laterally towards the same side as the pulled deflection wire 80. As can be understood from FIG. 34, which is an isometric view of one embodiment of the spring 300, due to configuration of the spring 300, which is laser cut from a metal cylinder, the spring 300 is uniplanar. As a result, the spring 300 will only deflect bi-directionally in a single plane.

In a manner similar to the deflection wires, the conductor wires 85 exit the core wall lumens 30 and extend distally to the end ring 310 adjacent to the inner circumferential surface of the cylindrical uniplanar spring 300. The conductor wires 85 transmit an electrical current from and to the end ring 310, which is used for medical diagnosis and/or treatment.

As shown in FIG. 30, the elastomeric tube 305 extends distally from a point just proximal of the rim 315 of the core 20 to a distal edge of a rim 325 of the end ring 310. In doing so, the elastomeric tube 305 surrounds the outer circumferential surface of the spring 300, the proximal outer circumferential surface of the end ring 310, and the distal outer circumferential surface 65 of the core 20. The outer polymer layer or tube 60 extends proximally from a point just proximal of the rim 315 of the core 20. In doing so, the outer polymer tube 60 surrounds the distal outer circumferential surface of the elastomeric tube 305 and the outer circumferential surface 65 of the core 20. In an overlapping area $A_O$, the aforementioned elements 20, 300, 305, 60 overlap to form a sandwich layer comprising, from inner to outer layer, the core 20, the spring 300, the elastomeric tube 305, and the outer polymer tube 60.

As can be understood from FIG. 30, the core 20 provides the strength and rigidity to maneuver the tubular body 10, the spring 300 provides the flexibility to allow the distal end 35 to deflect, the elastomeric tube 305 provides a flexible skin over the spring 300, and the outer polymer tube holds or sandwiches these elements together in the overlapping area $A_O$.

In manufacturing the large diameter tubular body 10 depicted in FIG. 30, a core 20 with a first outer diameter $D_O$ is extruded from a polymer such as PTFE. In extruding the core 20, core wall lumens 30 are formed in the radial thickness $T_R$ of the core wall 25. The core 20 is pulled over a mandrel.

The distal end 35 of the core 20 is ground or other wise treated to provide a second or reduced outer diameter $D_R$ to form the stepped distal end 35 shown in FIG. 31. The core now has a full diameter core section 20' that extends the majority of its length and a reduced diameter core section 20" at its distal end 35 (see FIG. 32). The cylindrical uniplanar spring 300 is placed over the reduced outer diameter $D_R$. The deflection and conductor wires 80, 85, which are coupled (e.g., welded) to the end ring 310, are inserted into their respective core wall lumens 30, and the end ring 310 is coupled (e.g., welded) to the distal end of the spring 300. The elastomeric tube 305 is pulled over the spring 300 and the distal most section of the first outer diameter $D_O$ of the core 20. The outer polymer tube 60 is pulled or extruded over the distal end of the elastomeric tube 305 and the full diameter core section 20'. The outer polymer tube 60, which is PEBAX in one embodiment, is reflowed to bond to the outer circumferential surfaces of the elastomeric tube 305 and the core 20, thereby holding the aforementioned elements 20, 300, 305, 60 together as an integral tubular body 10.

Although the present invention has been described with reference to preferred embodiments, persons skilled in the art will recognize that changes may be made in form and detail without departing from the spirit and scope of the invention.

What is claimed is:

1. A method of forming a tubular body for a catheter, sheath or lead without a mandrel, the tubular body being configured for insertion into the body lumen of a patient during a medical procedure, the method comprising:
    extruding a polymer core having a core wall with an inner circumferential surface and an outer circumferential surface, a first lumen, and a second lumen, wherein the inner circumferential surface of the core wall defines a first lumen and the second lumen is disposed between the inner circumferential surface and the outer circumferential surface, wherein the core wall, first lumen, and second lumen are integrally formed when extruding the polymer core, and wherein the first lumen and the second lumen extend longitudinally through a radial thickness of the core wall;
    forming a first layer and subsequently placing the first layer over an outer circumferential surface of the extruded polymer core; and
    bonding the first layer to the circumferential surface of the extruded polymer core via a reflow process, wherein the first and second lumen are mandrel free and a temperature of the reflow process is below a softening point of the polymer core to maintain a collapse free first and a second lumen.

2. The method of claim 1, further comprising:
    subsequent to placing a first layer over an outer circumferential of the extruded polymer core and prior to bonding the first layer to the circumferential surface of the extruded polymer core via a reflow process, placing a heat-shrinkable tube over the first layer.

3. The method of claim 1, wherein the polymer core is polytetrafluoroethylene (PTFE).

4. The method of claim 1, wherein the first layer is a reinforcement layer.

5. The method of claim 1, wherein the core wall is at least approximately 0.003 inch.

6. The method of claim 1, wherein the core wall is a circumferentially continuous core wall.

7. The method of claim 1, wherein the first lumen is a central lumen.

8. The method of claim 1, wherein the second lumen comprises a plurality of lumens evenly distributed about the circumference of the core wall.

9. A method of forming a tubular body for a catheter, sheath or lead without a mandrel, the tubular body being configured for insertion into the body lumen of a patient during a medical procedure, the method comprising:
    extruding a polymer core having a core wall with an inner circumferential surface and an outer circumferential surface, a first lumen, and a second lumen, wherein the inner circumferential surface of the core wall defines a first lumen and the second lumen is disposed between the inner circumferential surface and the outer circumferential surface, wherein the core wall, first lumen, and second lumen are integrally formed when extruding the polymer core, and wherein the first lumen and the second lumen extend longitudinally through a radial thickness of the core wall;
    forming a first layer and subsequently placing the first layer over an outer circumferential surface of the extruded polymer core; and
    bonding the first layer to the circumferential surface of the extruded polymer core via a reflow process, wherein the first and second lumen are mandrel free, a temperature of the reflow process is below a softening point of the polymer core, and the polymer core has an diameter between approximately 0.03 inch and approximately 0.50 inch and the core wall has a radial thickness of between approximately 0.003 inch and approximately 0.030 inch to maintain a collapse free first and second lumen during the reflow process.

10. The method of claim 9, further comprising:
    subsequent to placing a first layer over an outer circumferential of the extruded polymer core and prior to bonding the first layer to the circumferential surface of the extruded polymer core via a reflow process, placing a heat-shrinkable tube over the first layer.

11. The method of claim 9, wherein the polymer core is polytetrafluoroethylene (PTFE).

12. The method of claim 9, wherein the first layer is a reinforcement layer.

13. The method of claim 9, wherein the first lumen is a central lumen.

14. The method of claim 9, wherein the second lumen comprises a plurality of lumens evenly distributed about the circumference of the core wall.

* * * * *